United States Patent
Masuda

(10) Patent No.: US 7,766,929 B2
(45) Date of Patent: Aug. 3, 2010

(54) SURGICAL OPERATING APPARATUS

(75) Inventor: Shinya Masuda, Hino (JP)

(73) Assignee: Olympus Medical Systems Corp. (JP)

( * ) Notice: Subject to any disclaimer, the term of this patent is extended or adjusted under 35 U.S.C. 154(b) by 257 days.

(21) Appl. No.: 11/864,047

(22) Filed: Sep. 28, 2007

(65) Prior Publication Data
US 2009/0088667 A1 Apr. 2, 2009

(51) Int. Cl.
*A61B 17/32* (2006.01)
(52) U.S. Cl. .......................... 606/169; 604/22
(58) Field of Classification Search .............. 606/169, 606/171; 601/2; 604/22
See application file for complete search history.

(56) References Cited

U.S. PATENT DOCUMENTS

| | | | | |
|---|---|---|---|---|
| 6,669,690 B1 * | 12/2003 | Okada et al. | ................ | 606/40 |
| 2003/0135136 A1 * | 7/2003 | Murakami | ................ | 601/2 |
| 2006/0241532 A1 | 10/2006 | Murakami | | |

FOREIGN PATENT DOCUMENTS

EP  2 042 113  4/2009

JP  2003-265496  9/2003

OTHER PUBLICATIONS

Extended European Search Report dated Sep. 4, 2009 in corresponding European Patent Application No. EP 08 01 6274 (English language).
Letter from German associate dated Sep. 8, 2009 forwarding the Extended European Search Report dated Sep. 4, 2009 to Japanese associate, including discussion of relevancy thereof. German associate's letter dated Sep. 8, 2009 was date stamped received by Japanese associate on Sep. 11, 2009 (English language).

* cited by examiner

*Primary Examiner*—Anhtuan T Nguyen
*Assistant Examiner*—Tin Nguyen
(74) *Attorney, Agent, or Firm*—Ostrolenk Faber LLP

(57) ABSTRACT

A surgical tool includes a sheath, a probe body, a distal end portion and a proximal end portion. A probe distal end portion is provided at the distal end portion of the probe body, a jaw is rotatably supported on the distal end portion of the sheath and is engaged with the probe distal end portion. A first tubular member a fits on the proximal end portion of the sheath and extends rearward. It has an elongated slit and extends in an axial direction of the sheath. A second tubular member fits in a rear end portion of the first tubular member. A tubular driving member is slidably inserted in the sheath and rotates the jaw. A coupling member including a projection body passes through the second tubular member, includes an engaging portion which is engaged in the slit of the first tubular member.

6 Claims, 31 Drawing Sheets

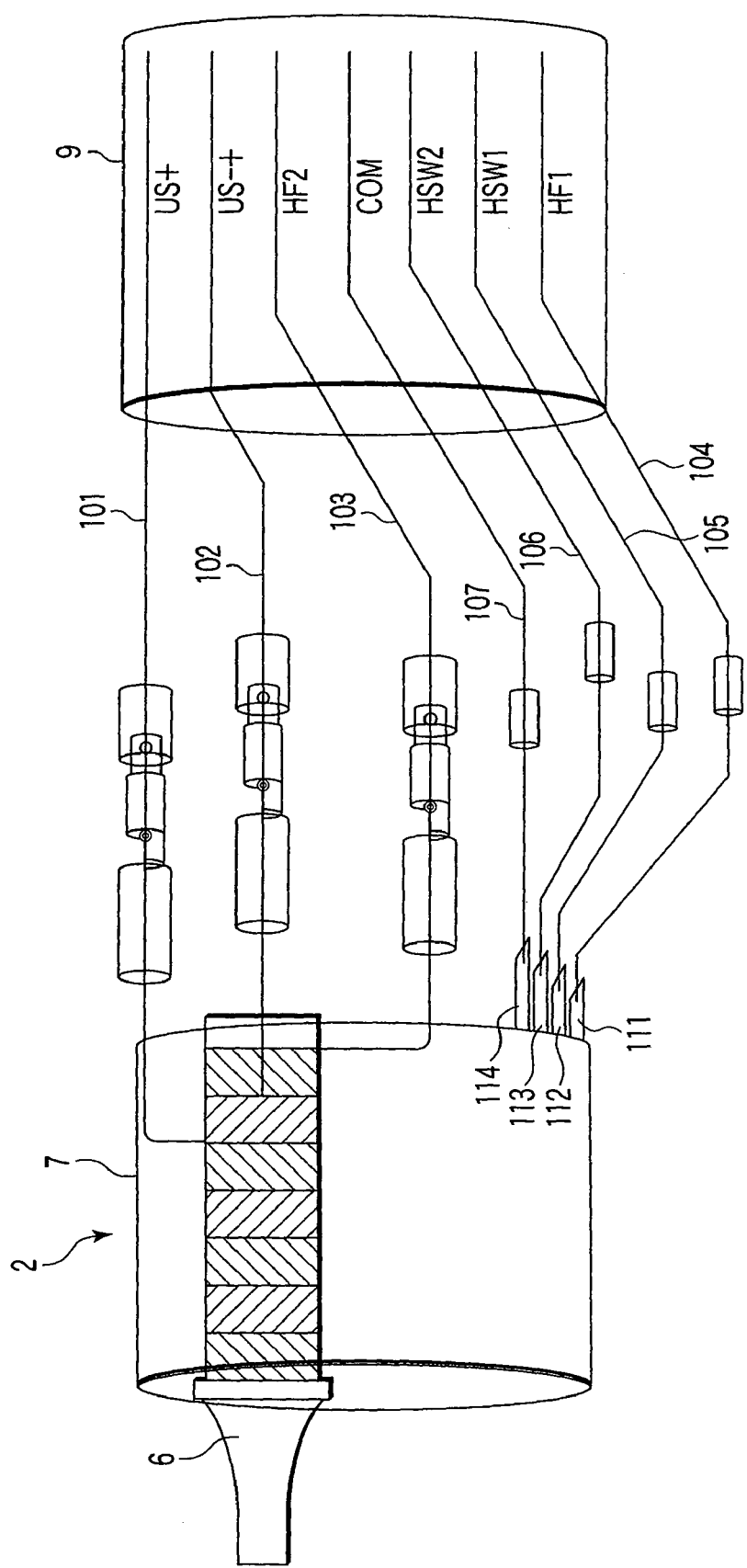
F I G. 52

SURGICAL OPERATING APPARATUS

BACKGROUND OF THE INVENTION

The present invention relates to a surgical operating apparatus that includes a probe, in which ultrasonic vibration is transmitted, and a jaw which is engageable with the probe, and performs therapeutic treatment, such as incision, resection or coagulation, of a living body tissue, which is clamped between the probe and the jaw, by making use of composite energy of ultrasonic and high-frequency waves.

Jpn. Pat. Appln. KOKAI Publication No. 2003-265496 (Patent Document 1), for instance, discloses a general example of an ultrasonic therapeutic apparatus which performs therapeutic treatment, such as incision, resection or coagulation, of a living body tissue by making use of ultrasonic.

In this apparatus, a proximal-side operation section is coupled to a proximal end portion of an elongated insertion section. An ultrasonic transducer which generates ultrasonic vibration is provided in the operation section. A therapeutic section for treating a living body tissue is provided at a distal end portion of the insertion section.

The insertion section has an elongated tubular sheath. A rod-shaped vibration transmission member (probe) is inserted in the sheath. A proximal end portion of the vibration transmission member is detachably attached to the ultrasonic transducer via a screw-type coupling section. Ultrasonic vibration, which is generated by the ultrasonic transducer, is transmitted to a probe distal end portion at the distal end side of the vibration transmission member.

In the therapeutic section, a jaw is provided so as to be opposed to the probe distal end portion. A proximal end portion of the jaw is rotatably supported on a distal end portion of the sheath via a support shaft. An operation rod for driving the jaw is inserted in the sheath so as to be axially advancible/retreatable.

The operation section is provided with an operation handle and a rotation knob. The operation handle includes a stationary handle and a movable handle. A proximal end portion of the sheath is detachably coupled to the stationary handle. A proximal end portion of the operation rod is detachably coupled to the movable handle. In accordance with the operation of the movable handle of the operation handle, the operation rod is axially advanced/retreated. In interlock with the operation of the operation rod, the jaw is opened/closed relative to the probe distal end portion.

At this time, a living body tissue is held between the probe distal end portion and the jaw in accordance with the closing operation of the jaw. In this state, ultrasonic vibration from the ultrasonic transducer is transmitted to the probe distal end portion on the therapeutic section side via the vibration transmission member. Thereby, using ultrasonic, therapeutic treatment, such as incision, resection or coagulation, of the living body tissue is performed.

In addition, in accordance with the operation of the rotation knob, the probe distal end portion and the jaw of the therapeutic section are rotated at the same time in the same direction about the axis.

In the apparatus of Patent Document 1, a sheath attachment/detachment section for detachably coupling the proximal end portion of the sheath to the stationary handle and an operation section attachment/detachment section for detachably coupling the proximal end portion of the operation rod to the movable handle are independently provided. Consequently, the number of structural parts within the operation section increases, and the internal structure of the operation section becomes complex. Thus, there is a problem that the assembly work is difficult and the manufacturing cost is high.

BRIEF SUMMARY OF THE INVENTION

The present invention has been made in consideration of the above-described circumstances, and the object of the invention is to provide a surgical operating apparatus which can easily be assembled and can be manufactured at low cost.

A surgical operating apparatus in one aspect of the present invention comprises: a sheath having a distal end portion and a proximal end portion; a shaft-shaped probe body which is inserted in the sheath and has a distal end portion and a proximal end portion, and in which ultrasonic vibration is transmitted; a probe distal end portion which is provided at the distal end portion of the probe body; a jaw which is rotatably supported on the distal end portion of the sheath and is engaged with the probe distal end portion; a first tubular member having a tubular body which is fitted on the proximal end portion of the sheath and extends rearward, and has an elongated slit which is provided in an outer peripheral wall portion of the tubular body and extends in an axial direction of the sheath; a second tubular member which is fitted in a rear end portion of the first tubular member; a tubular driving member which is inserted in the sheath slidably in the axial direction of the sheath, and rotates the jaw by sliding movement thereof; and a coupling member including a projection body projecting outward of the driving member, the projection body being passed through the second tubular member, thus forming a coupling body which couples the driving member and the second tubular member, the coupling member including an engaging portion which is engaged in the slit of the first tubular member, the coupling member coupling the coupling body slidably as one body, relative to the first tubular member, along the slit in the axial direction of the sheath.

Preferably, the surgical operating apparatus includes a handle unit which is detachably coupled to the proximal end portion of the sheath, the handle unit includes a stationary handle and a movable handle which is coupled rotatably about a rotational shaft relative to the stationary handle, the first tubular member includes a first attachment/detachment section which is detachably coupled to the stationary handle, and the second tubular member includes a second attachment/detachment section which is detachably coupled to the movable handle.

Preferably, the sheath includes, at the proximal end portion thereof, a flare portion which has a greater inside diameter than the other portion thereof, and seal means for effecting sealing between the sheath and the driving member is provided between the flare portion and the driving member.

Preferably, the seal means includes a pair of backup rings, which are paired in a back-and-forth direction along the axial direction of the sheath, and an O ring which is provided between the backup rings so as to be movable in the axial direction of the sheath.

Preferably, the second tubular member has a through-hole in which the projection body of the coupling member is passed through, and the projection body has a threaded portion which is screwed and coupled in the through-hole.

Preferably, the second tubular member has a through-hole in which the projection body of the coupling member is passed through, and the projection body has, at a part of a penetration portion which is passed through the through-hole, a press-fitting portion which is press-fitted in the through-hole.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 52 is a schematic view showing an internal structure of a cable of the transducer unit of the ultrasonic therapeutic apparatus according to the first embodiment;

DETAILED DESCRIPTION OF THE INVENTION

Figure 1:
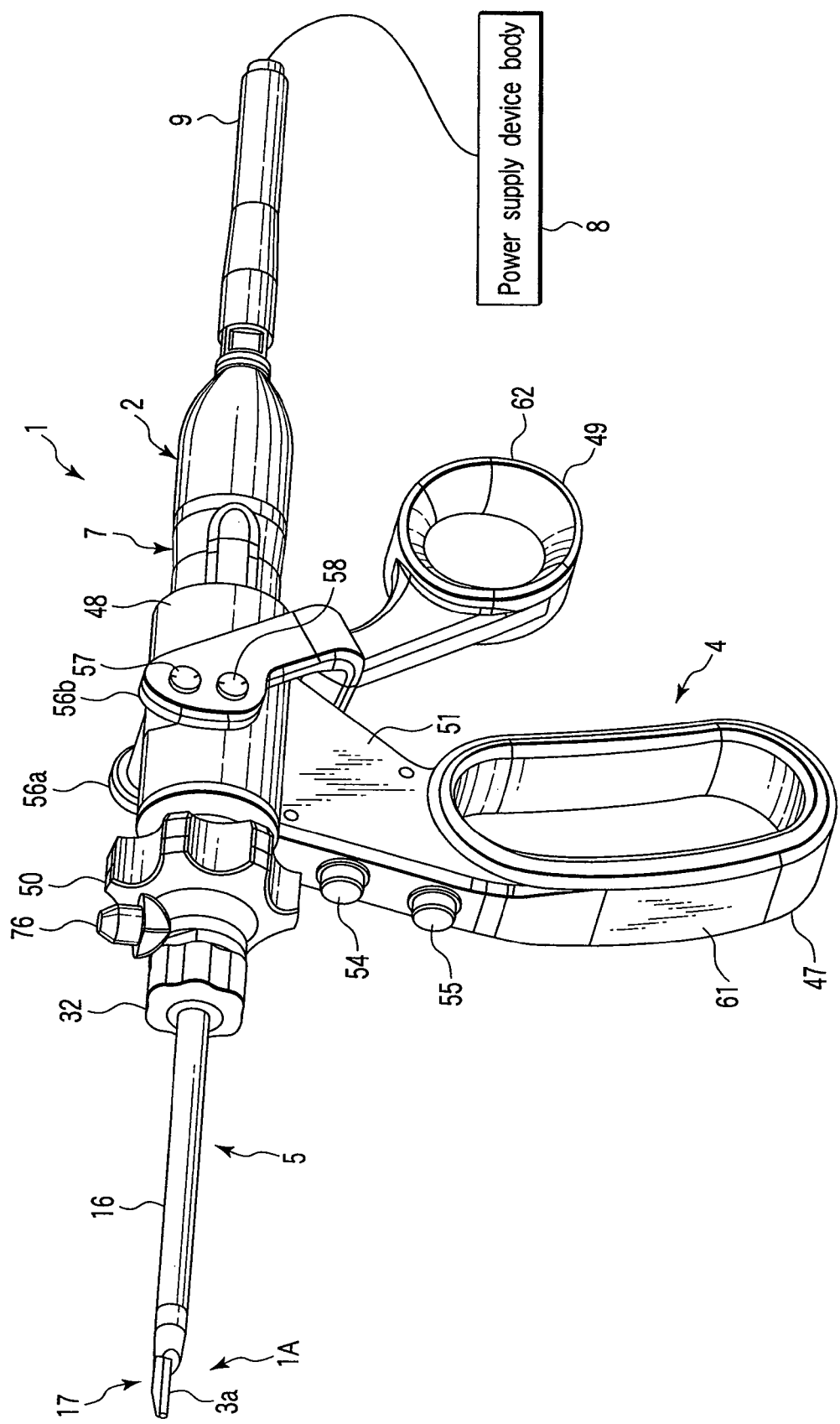
FIG. 1 is a perspective view that schematically shows the entire structure of an ultrasonic therapeutic apparatus according to a first embodiment of the present invention.

A first embodiment of the present invention will now be described with reference to FIG. 1 to FIG. 52. FIG. 1 schematically shows the entire structure of a handpiece 1 of an ultrasonic therapeutic apparatus which is a surgical operating apparatus according to the first embodiment. The ultrasonic therapeutic apparatus of the present embodiment is an ultrasonic coagulation/incision apparatus. This ultrasonic coagulation/incision apparatus can perform therapeutic treatment, such as incision, resection or coagulation, of a living body tissue by making use of ultrasonic, and can also perform therapeutic treatment by high-frequency waves.

Figure 2:
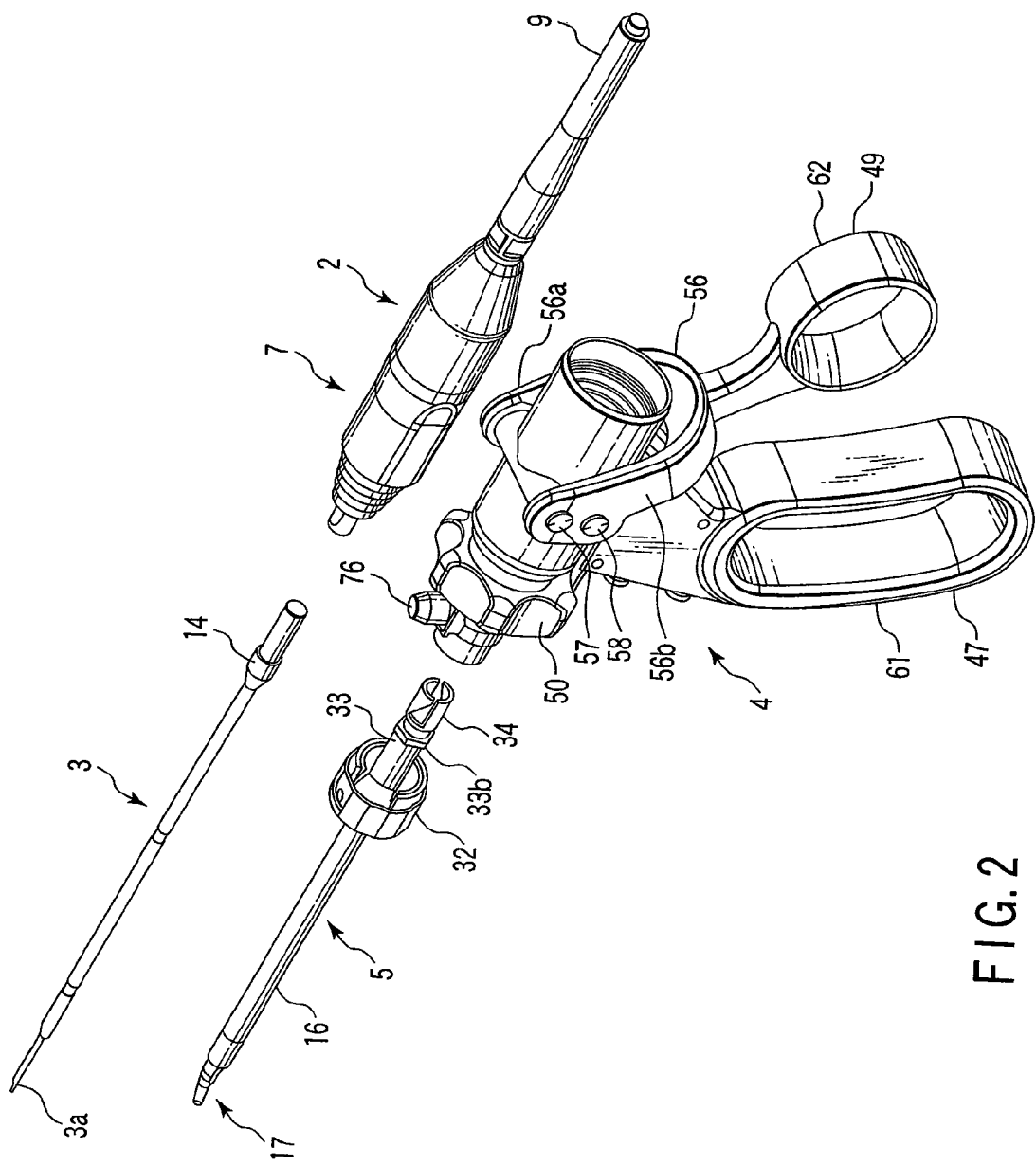
FIG. 2 is a perspective view showing a disassembled state of the ultrasonic therapeutic apparatus according to the first embodiment, with coupling sections of assembly units of the ultrasonic therapeutic apparatus being disconnected.

The handpiece 1, as shown in FIG. 2, comprises four units, namely, a transducer unit 2, a probe unit (probe section) 3, a handle unit (operation section) 4 and a sheath unit (sheath section) 5. These units are detachably coupled.

Figure 4:
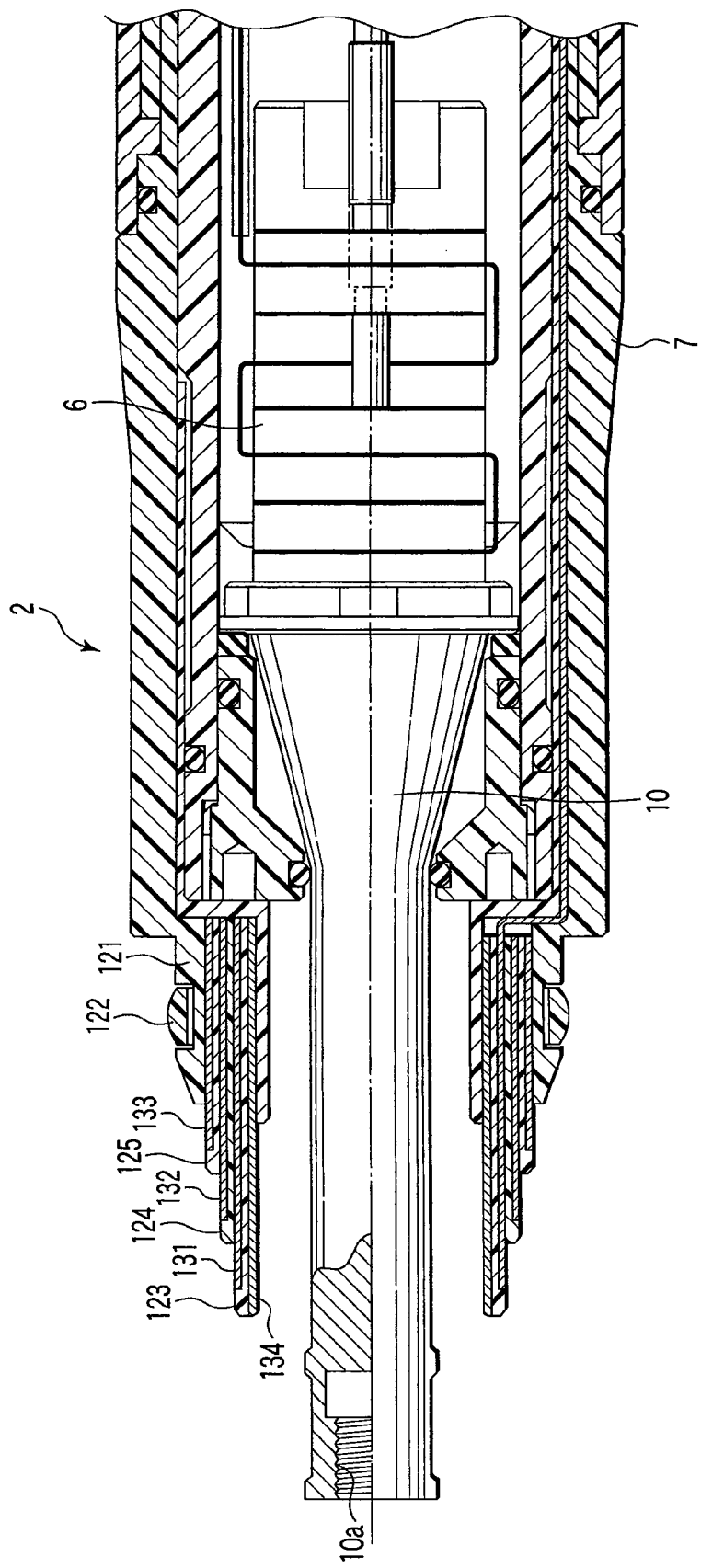
FIG. 4 is a longitudinal cross-sectional view showing an internal structure of the transducer unit of the ultrasonic therapeutic apparatus according to the first embodiment.

As shown in FIG. 4, an ultrasonic transducer 6 for generating ultrasonic vibration by a piezoelectric oscillator, which converts an electric current to ultrasonic vibration, is built in the transducer unit 2. An outside of the ultrasonic transducer 6 is covered with a cylindrical transducer cover 7. As shown in FIG. 1, a cable 9 for supplying an electric current for generating ultrasonic vibration from a power supply device body 8 extends from a rear end of the transducer unit 2.

A proximal end portion of a horn 10, which increases the amplitude of ultrasonic vibration, is coupled to a front end portion of the ultrasonic transducer 6. A screw hole portion 10a for attaching the probe is formed at a distal end portion of the horn 10.

Figure 5:
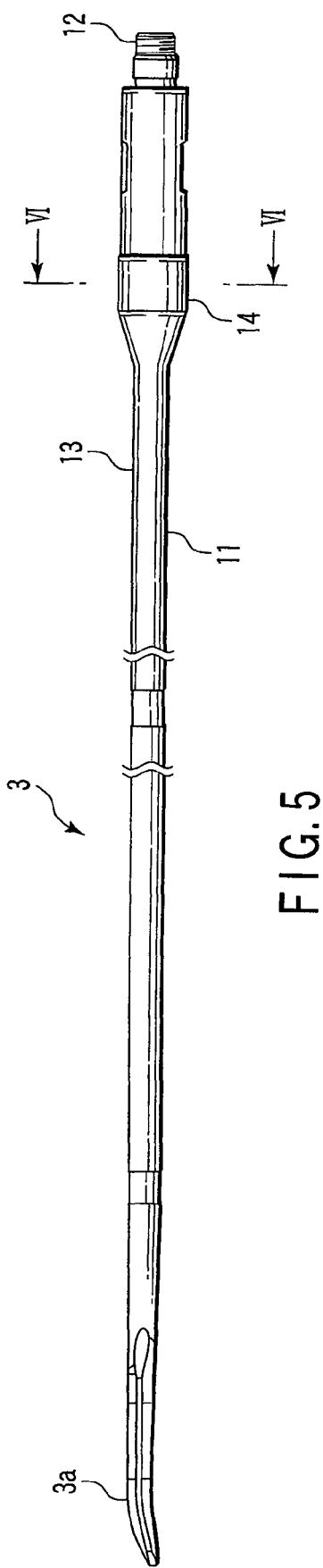
FIG. 5 is a plan view showing a probe unit of the ultrasonic therapeutic apparatus according to the first embodiment.

FIG. 5 shows the external appearance of the entire probe unit 3. The probe unit 3 is designed such that the entire length thereof may become an integer number of times of half-wave length of the ultrasonic vibration. The probe unit 3 has a distal end portion and a proximal end portion, and includes a metallic rod-shaped vibration transmission member 11 having a long axis. A proximal end portion of the vibration transmission member 11 is provided with a screw portion 12 which is to be engaged with the screw hole portion 10a of the horn 10. The screw portion 12 is engaged with the screw hole portion 10a of the horn 10 of the transducer unit 2. Thereby, the probe unit 3 and the transducer unit 2 are assembled. At this time, a first high-frequency electric path 13, through which a high-frequency current is transmitted, is formed in the coupled body of the ultrasonic transducer 6 and the probe unit 3.

Figure 7:
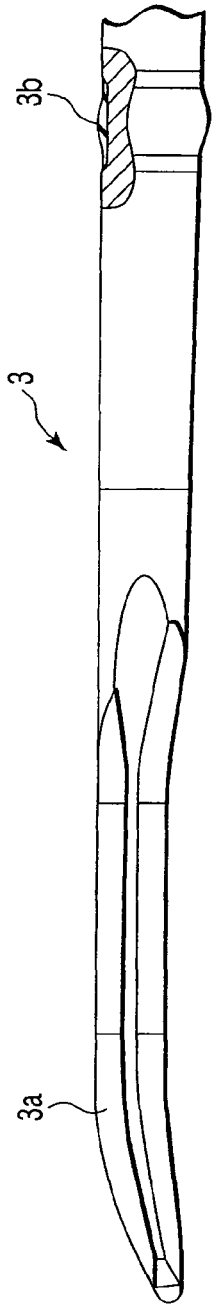
FIG. 7 is a plan view showing a distal end portion of the probe unit of the ultrasonic therapeutic apparatus according to the first embodiment.

A probe distal end portion 3a is provided at a distal end portion of the vibration transmission member 11. The probe distal end portion 3a is formed in a substantially J-shaped curved form. The probe distal end portion 3a constitutes a first electrode section which is one of bipolar electrodes. The cross-sectional area of the probe unit 3 is decreased in the axial direction at several nodes of vibration in the axial direction, so that an amplitude necessary for therapeutic treatment can be obtained at the probe distal end portion 3a. Rubber rings 3b (see FIG. 7), which are formed of elastic material in an annular shape, are attached to several positions of nodes of vibration along the axial direction of the probe unit 3. The rubber rings 3b prevent interference between the probe unit 3 and the sheath unit 5.

Figure 6:
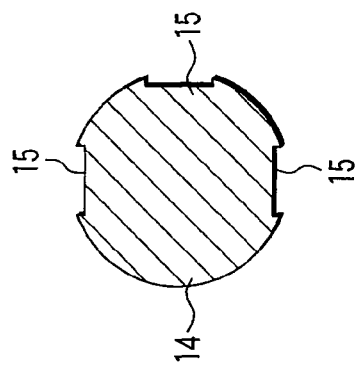
FIG. 6 is a cross-sectional view taken along line VI-VI in FIG. 5.

A flange portion 14 is provided at the position of the node of vibration on the most proximal end side in the axial direction of the probe unit 3. As shown in FIG. 6, engaging recess portions 15 each having a key groove shape are formed on the outer peripheral surface of the flange portion 14 at three positions in the circumferential direction thereof.

Figure 8B:
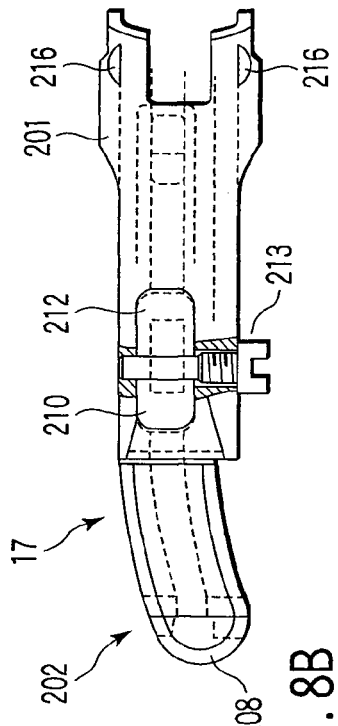
FIG. 8B is a plan view showing a jaw of the sheath unit of the ultrasonic therapeutic apparatus according to the first embodiment.
Figure 8A:
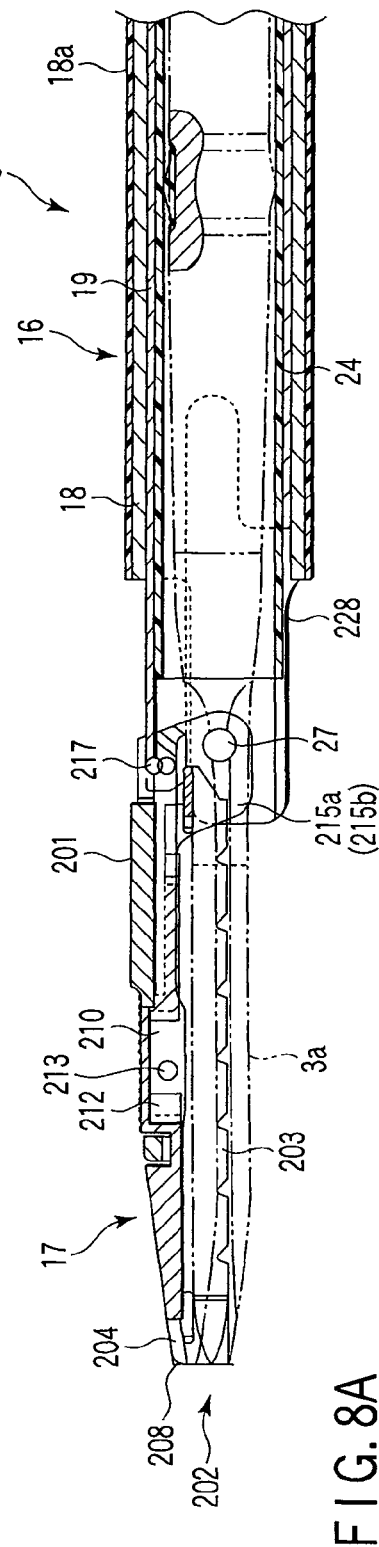
FIG. 8A is a longitudinal cross-sectional view showing a distal end portion of a sheath unit of the ultrasonic therapeutic apparatus according to the first embodiment.
Figure 9A:
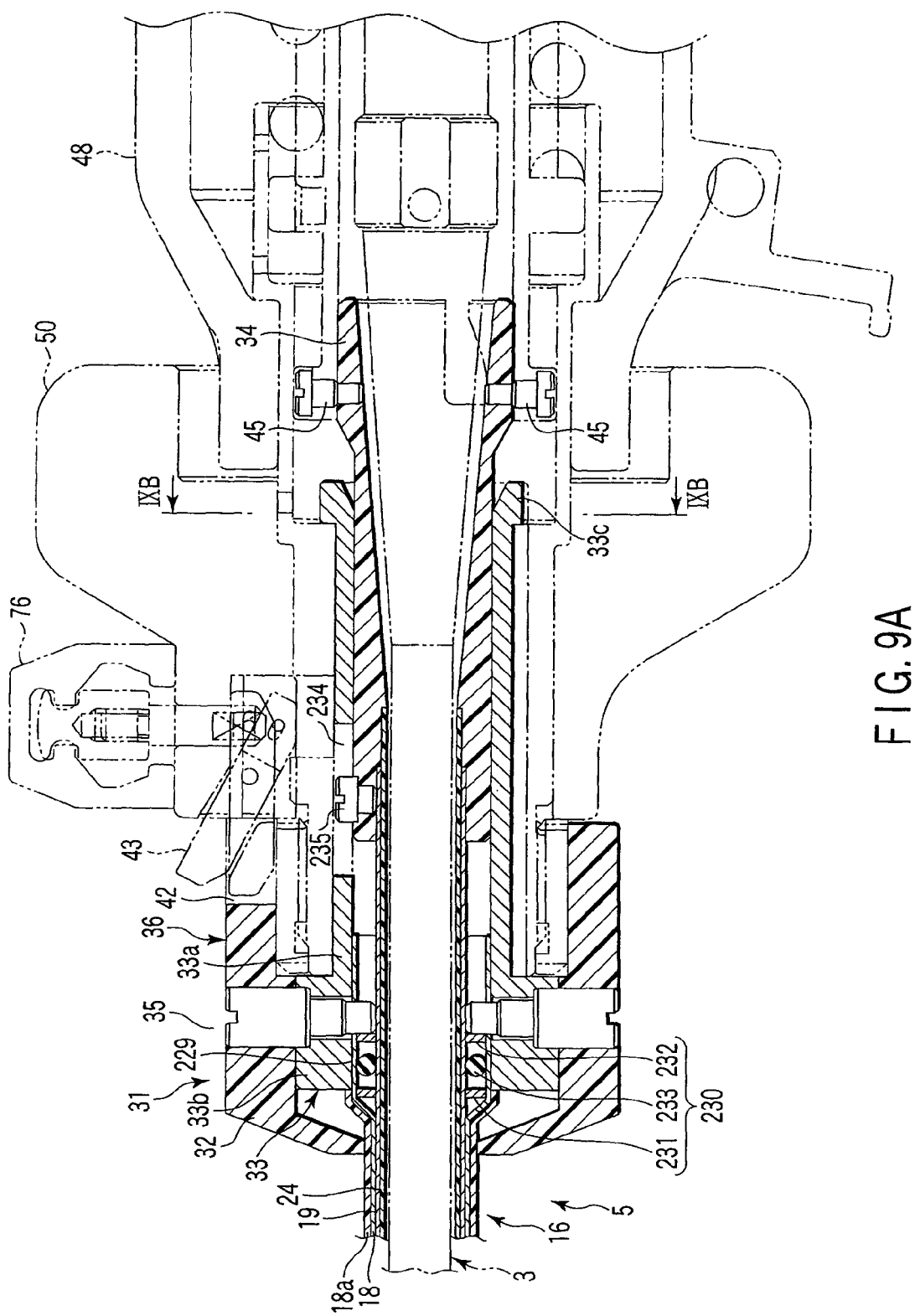
FIG. 9A is a longitudinal cross-sectional view showing a proximal end portion of the sheath unit of the ultrasonic therapeutic apparatus according to the first embodiment.

FIG. 8A shows a distal end portion of the sheath unit 5, and FIG. 9A shows a proximal end portion of the sheath unit 5. As shown in FIG. 8A, the sheath unit 5 includes a sheath body 16, which is formed of a cylindrical body, and a jaw 17 which is provided at a distal end of the sheath body 16. The sheath body 16 includes a metallic sheath 18 which is an outer cylinder, and a metallic driving pipe 19 which is an inner cylinder. The driving pipe 19 is axially movably inserted in the sheath 18.

As shown in FIG. 8A, the outer peripheral surface of the sheath 18 is covered with an outer coating 18a which is formed of an insulating material such as a resin. An insulation tube 24, which is formed of an insulating material, is provided on the inner peripheral side of the driving pipe 19.

Figure 10:
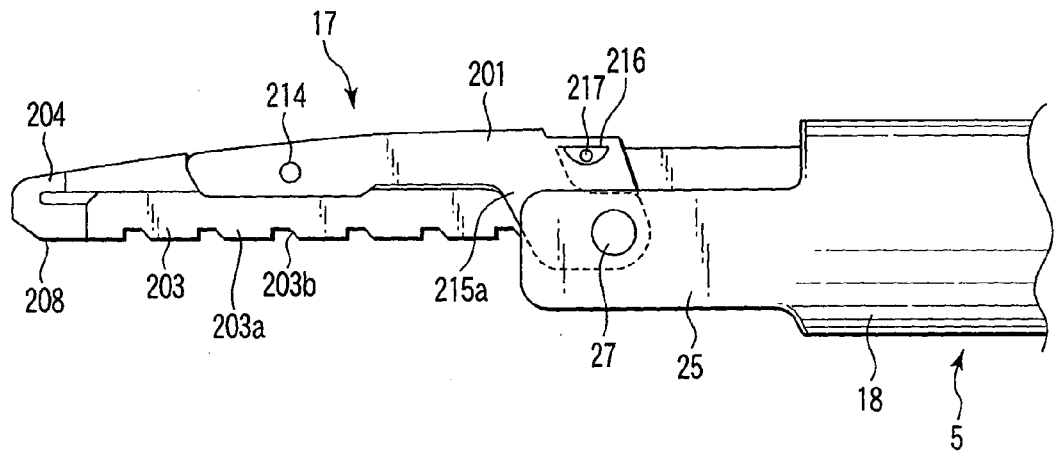
FIG. 10 is a side view showing an attachment section of the jaw of the ultrasonic therapeutic apparatus according to the first embodiment.
Figure 11:
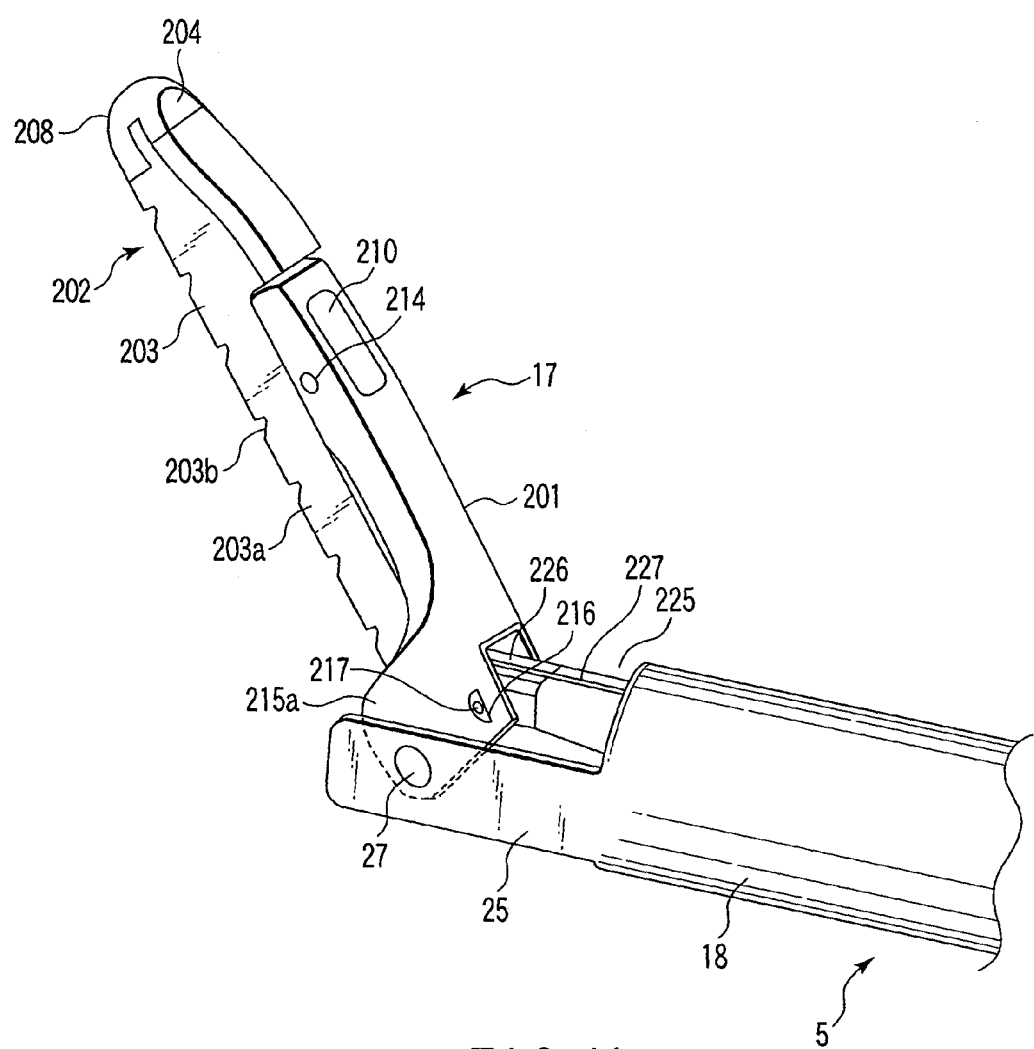
FIG. 11 is a perspective view showing a state in which the jaw of the ultrasonic therapeutic apparatus according to the first embodiment is opened.
Figure 12:
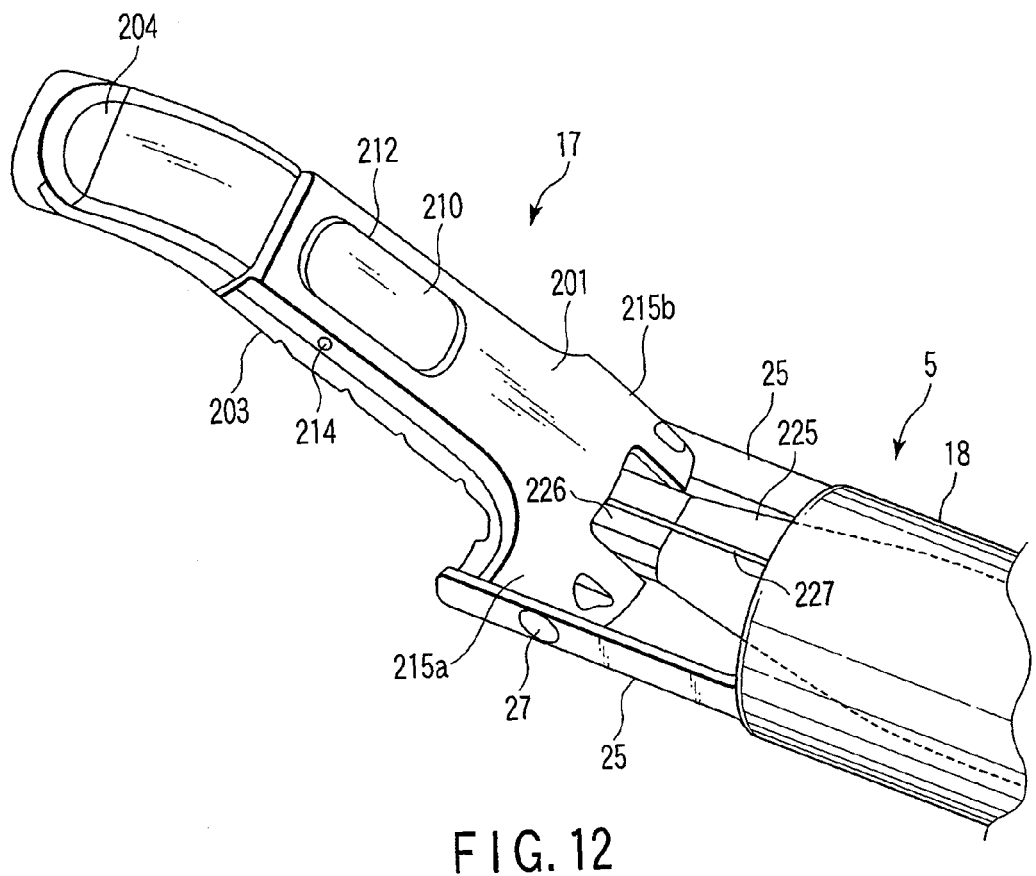
FIG. 12 is a perspective view showing, in a direction different from the direction in FIG. 11, the state in which the jaw of the ultrasonic therapeutic apparatus according to the first embodiment is opened.
Figure 13:
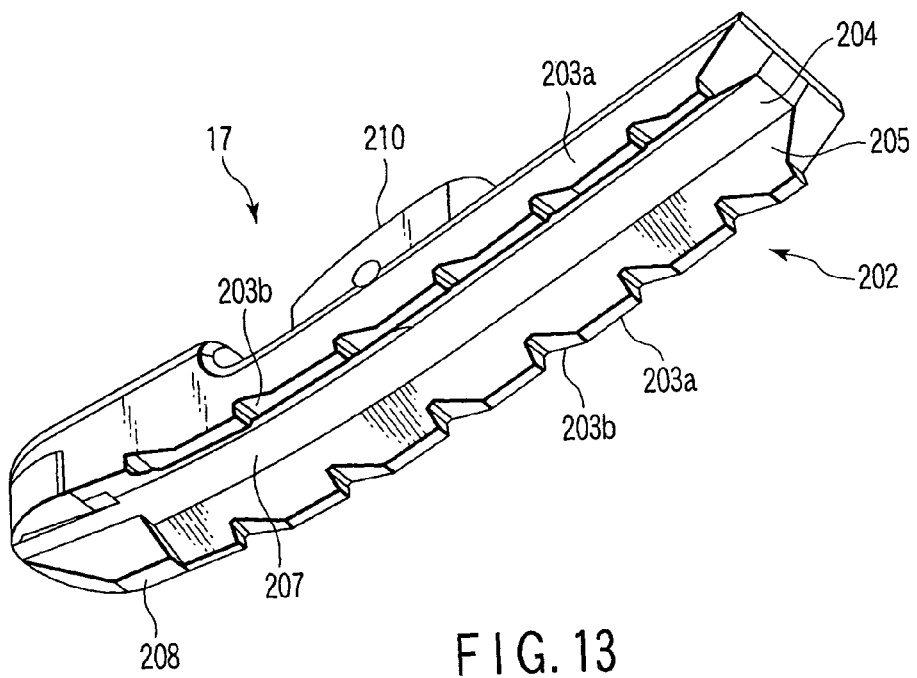
FIG. 13 is a perspective view showing a hold member of the jaw of the ultrasonic therapeutic apparatus according to the first embodiment.

As shown in FIGS. 10 to 12, a pair of right and left projection portions 25 are provided at a distal end portion of the sheath 18 so as to project in a forward direction of the sheath 18. A proximal end portion of the jaw 17 is rotatably attached to the projection portions 25 via a support pin 27. When the probe unit 3 and the sheath unit 5 are assembled, the jaw 17 is positioned to be opposed to the probe distal end portion 3a of the probe unit 3.

As shown in FIG. 8B, the jaw 17 is formed in a substantially J-shaped curved form, which corresponds to the curved shape of the probe distal end portion 3a, in accordance with the curved shape of the probe distal end portion 3a of the probe unit 3. The jaw 17 is configured to be rotated about the support pin 27 by the advancing/retreating movement of the driving pipe 19 in the axial direction. A therapeutic section 1A of the handpiece 1 is constituted by the jaw 17 and the probe distal end portion 3a.

Figure 14:
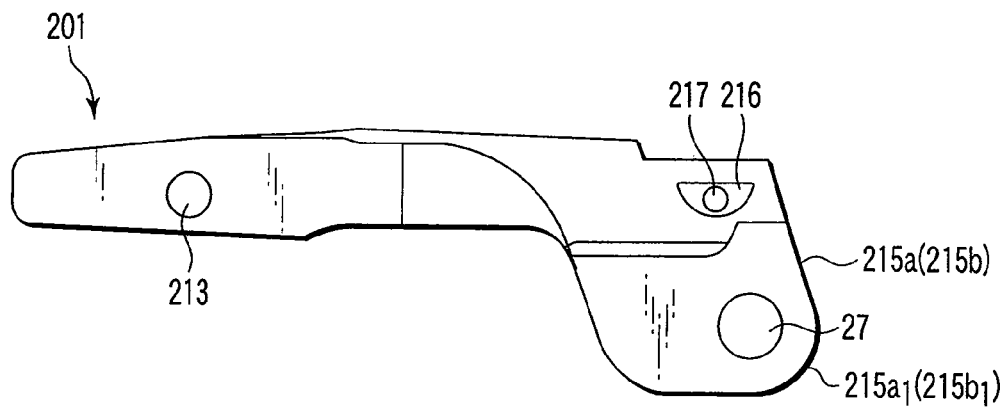
FIG. 14 is a side view showing a jaw body of the jaw of the ultrasonic therapeutic apparatus according to the first embodiment.
Figure 15:
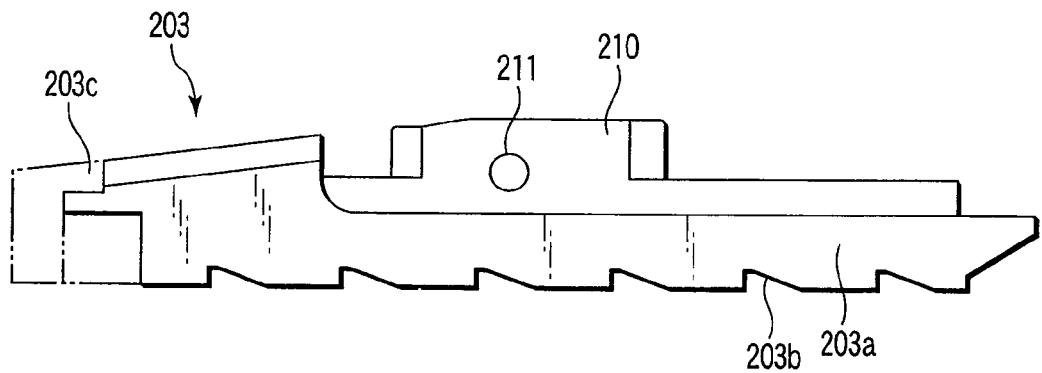
FIG. 15 is a side view showing an electrode member of the jaw of the ultrasonic therapeutic apparatus according to the first embodiment.

The jaw 17 includes a metallic jaw body 201 (see FIG. 14) which is an electrically conductive member, and a hold member 202 which is attached to the jaw body 201. The hold member 202 is composed of an electrode member 203 (see FIG. 15) for high-frequency therapeutic treatment, and an insulation member 204 (see FIG. 16) for ultrasonic therapeutic treatment. The electrode member 203 constitutes a second electrode section which is the other electrode of the bipolar electrodes.

Figure 17:
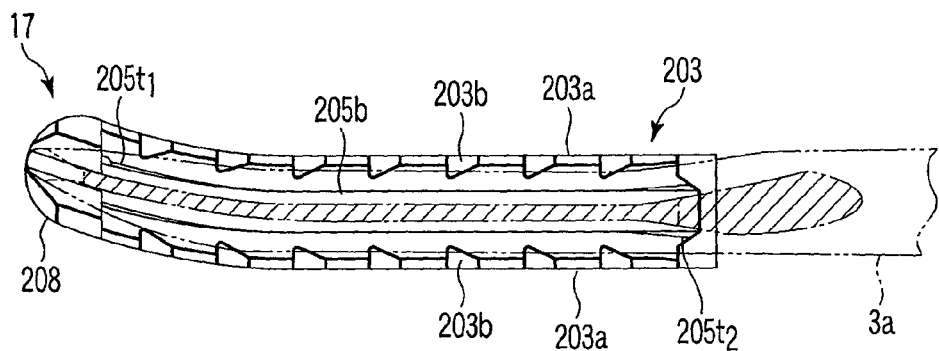
FIG. 17 is a plan view showing an engaged state between the electrode member of the jaw and the probe distal end portion of the ultrasonic therapeutic apparatus according to the first embodiment.
Figure 18:
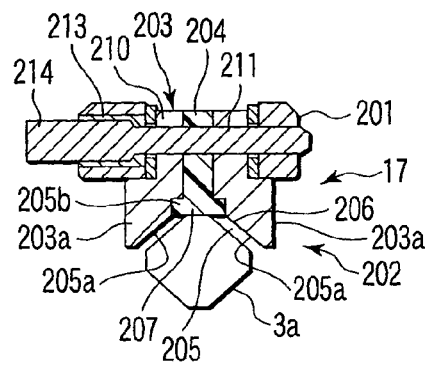
FIG. 18 is a vertical cross-sectional view showing an engaged state between the electrode member of the jaw and the probe distal end portion of the ultrasonic therapeutic apparatus according to the first embodiment.

As shown in FIGS. 17 and 18, a groove portion 205, which is formed in accordance with the curved shape of the probe distal end portion 3a, is formed on the lower surface of the electrode member 203. An engaging surface 206, which is to be engaged with the probe distal end portion 3a, is formed by the groove portion 205. A groove width W of the groove portion 205 is set in consideration of the diameter dimension of the probe distal end portion 3a. Specifically, the groove width W is set to be greater than the diameter dimension of the probe distal end portion 3a by a predetermined ratio, thereby preventing contact between the engaging surface 206 of the electrode member 203 and the probe distal end portion 3a.

Figure 19:
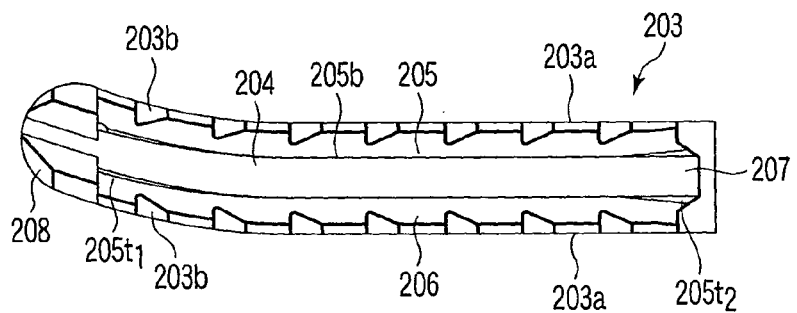
FIG. 19 is a plan view showing a living body tissue contact surface of the hold member of the jaw of the ultrasonic therapeutic apparatus according to the first embodiment.
Figure 20:
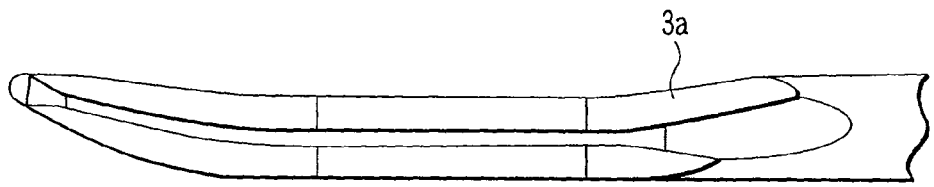
FIG. 20 is a plan view showing the probe distal end portion of the ultrasonic therapeutic apparatus according to the first embodiment.

Inclined surfaces 205a, which are configured to gradually increase the groove width toward a lower-side opening surface, as shown in FIG. 18, are formed on both side wall surfaces of the groove portion 205. In addition, as shown in FIG. 19, tooth portions 203b for preventing a slip are formed on both side walls 203a of the groove portion 205 on the lower-side opening surface side. The tooth portions 203b form a slip-preventing section for preventing a slip of a clamped object between the probe distal end portion 3a and the jaw 17 when the jaw 17 and probe distal end portion 3a are engaged. A wall thickness T of the electrode member 203 is properly determined in consideration of the rigidity and coagulation performance.

Further, in the electrode member 203, a notch portion 205b is formed at a bottom portion of the groove portion 205. The notch portion 205b is formed in accordance with the curved shape of the probe distal end portion 3a. A pad member 207, which is formed of an insulating material, for instance, a resin material such as polytetrafluoroethylene, is disposed in the notch portion 205b. As shown in FIG. 18, the pad member 207 is a probe contact member which is in contact with the probe distal end portion 3a. The probe distal end portion 3a comes in contact with the pad member 207, thus securing a clearance between the second electrode section of the electrode member 203 and the probe distal end portion 3a.

In addition, the jaw 17 has a block-shaped distal end chip 208 at a distal end portion of the engaging surface 206 for engagement with the probe distal end portion 3a. The distal end chip 208 is formed of an insulating material, for instance, a resin material such as polytetrafluoroethylene. When the jaw 17 and probe distal end portion 3a are engaged, a positional displacement relative to the probe distal end portion 3a is tolerated by the distal end chip 208.

Figure 16:
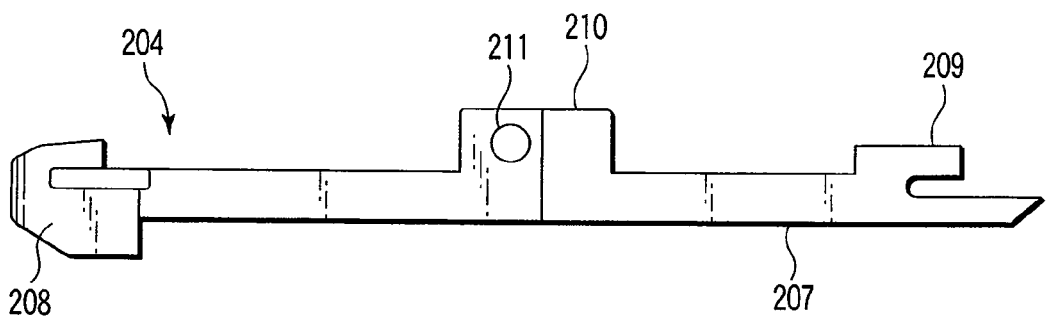
FIG. 16 is a side view showing an insulation member of the jaw of the ultrasonic therapeutic apparatus according to the first embodiment.

As shown in FIG. 16, in the insulation member 204, the distal end chip 208 is coupled to the distal end portion of the pad member 207. In the insulation member 204, the pad member 207 and the distal end chip 208 are provided as one body.

The electrode member 203 and insulation member 204 are integrally assembled to form the hold member 202. A hook-shaped engaging portion 209 is formed at a rear end portion of the insulation member 204. In addition, a distal end chip engaging portion 203c, which engages the distal end chip 208, is formed at the distal end portion of the electrode member 203. When the electrode member 203 and the insulation member 204 are assembled, the distal end chip 208 is engaged with the distal end chip engaging portion 203c, and also the engaging portion 209 at the rear end portion of the insulation member 204 is engaged with the rear end portion of the electrode member 203 in the state in which the pad member 207 is inserted in the notch portion 205b of the groove portion 205 of the electrode member 203.

A projection portion 210 for attachment is provided on that side of the hold member 202, which is opposed to the engaging surface 206 for engagement with the probe distal end portion 3a. A screw insertion hole 211 is formed in the projection portion 210.

A hold member engaging portion 212, which engages the projection portion 210 of the hold member 202, is provided on a distal end side of the jaw body 201. The hold member 202 is engaged with the hold member engaging portion 212. Further, a screw hole 213 is formed in side wall portions of the hold member engaging portion 212. As shown in FIG. 18, when the hold member engaging portion 212 of the jaw body 201 and the projection portion 210 of the hold member 202 are engaged, a fixing screw 214, which is engaged in the screw hole 213 of the jaw body 201, is inserted in the screw insertion hole 211 of the hold member 202. In this state, the fixing screw 214 is fastened in the screw hole 213, and thereby the hold member 202 is attached to the jaw body 201. The electrode member 203 of the hold member 202 and the jaw body 201 are electrically connected via the fixing screw 214.

A proximal end portion of the jaw body 201 has two-forked arm portions 215a and 215b. The respective arm portions 215a and 215b have extension portions 215a1 and 215b1, which extend obliquely downward from a position of a center line of the jaw body 201. The extension portions 215a1 and 215b1 are rotatably attached by the support pin 27 to the right and left projection portions 25 at the distal end portion of the sheath 18.

A coupling pin insertion hole 216 is formed in a proximal portion of each of the two arm portions 215a and 215b. A coupling pin 217 for coupling the jaw body 201 and the driving pipe 19 is inserted in the coupling pin insertion holes 216. The jaw body 201 and the driving pipe 19 are electrically connected via the coupling pin 217.

Thereby, the driving force of the driving pipe 19 is transmitted to the jaw 17 via the coupling pin 217 by the advancing/retreating in the axial direction of the driving pipe 19. Accordingly, the jaw 17 is rotated about the support pin 27. In this case, when the driving pipe 19 is pulled rearward, the jaw 17 is rotated about the support pin 27 and driven (to an open position) in a direction away from the probe distal end portion 3a. Conversely, when the driving pipe 19 is pushed forward, the jaw 17 is rotated about the support pin 27 and driven (to a closed position) in a direction toward the probe distal end portion 3a. A living body tissue is held between the jaw 17 and the probe distal end portion 3a of the probe unit 3 when the jaw 17 is rotated to the closed position.

The therapeutic section 1A of the handpiece 1 is constituted by the jaw 17 and the probe distal end portion 3a of the probe unit 3. The therapeutic section 1A is configured to selectively perform a plurality of therapeutic functions, for example, two therapeutic functions (a first therapeutic function and a second therapeutic function) in this embodiment. For instance, the first therapeutic function is set to be a function of simultaneously outputting an ultrasonic therapeutic output and a high-frequency therapeutic output. The second therapeutic function is set to be a function of outputting only the high-frequency therapeutic output.

The first therapeutic function and second therapeutic function of the therapeutic section 1A are not limited to the above-described configuration. For example, the first therapeutic function may be set to be a function of outputting an ultrasonic therapeutic output in a maximum output state, and the second therapeutic function may be set to be a function of outputting the ultrasonic therapeutic output in a preset arbitrary output state which is lower than the maximum output state.

As shown in FIGS. 17 and 19, the jaw 17 has, at a distal end portion of the groove portion 205, a distal-end-side groove width varying section 205t1 which has such a tapering shape that the groove width of the groove portion 205 gradually increases toward the distal end. In addition, the jaw 17 has, at a proximal end portion of the groove portion 205, a proximal-end-side groove width varying section 205t2 which has such a tapering shape that the groove width of the groove portion 205 gradually increases toward the proximal end. In the distal-end-side groove width varying section 205t1 and proximal-end-side groove width varying section 205t2, a positional displacement in assembly between the probe distal end portion 3a and the electrode member 203 of the jaw 17 can be tolerated in a case where the assembly position of the electrode member 203 of the jaw 17 is slightly displaced, relative to the probe distal end portion 3a, in the axial direction of the sheath unit 5 when the probe unit 3 and the sheath unit 5 are assembled.

Figure 21:
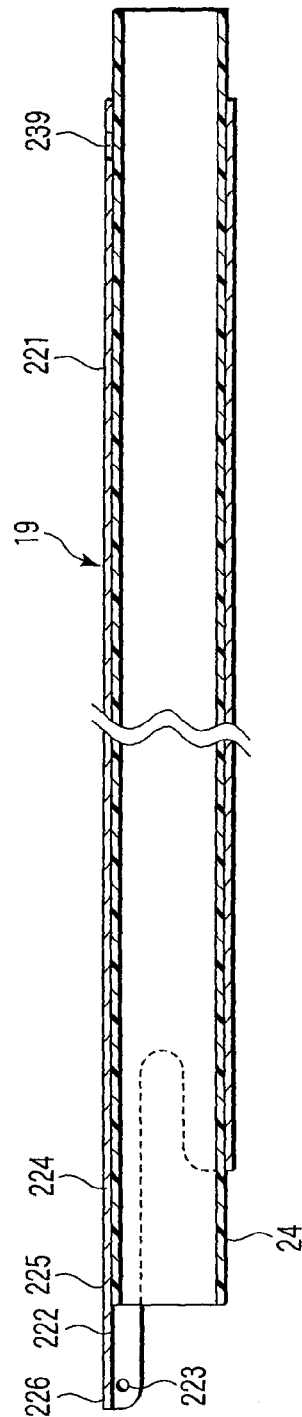
FIG. 21 is a longitudinal cross-sectional view showing a driving pipe of the ultrasonic therapeutic apparatus according to the first embodiment.

FIG. 21 shows the driving pipe 19. The driving pipe 19 includes a tubular body section 221 and an operating section 222. The body section 221 is inserted in the sheath 18 so as to be slidable in the axial direction of the sheath 18. The operating section 222 is disposed on the distal end side of the body section 221, and includes a connection section 223 which is connected to the jaw 17.

Figure 22:
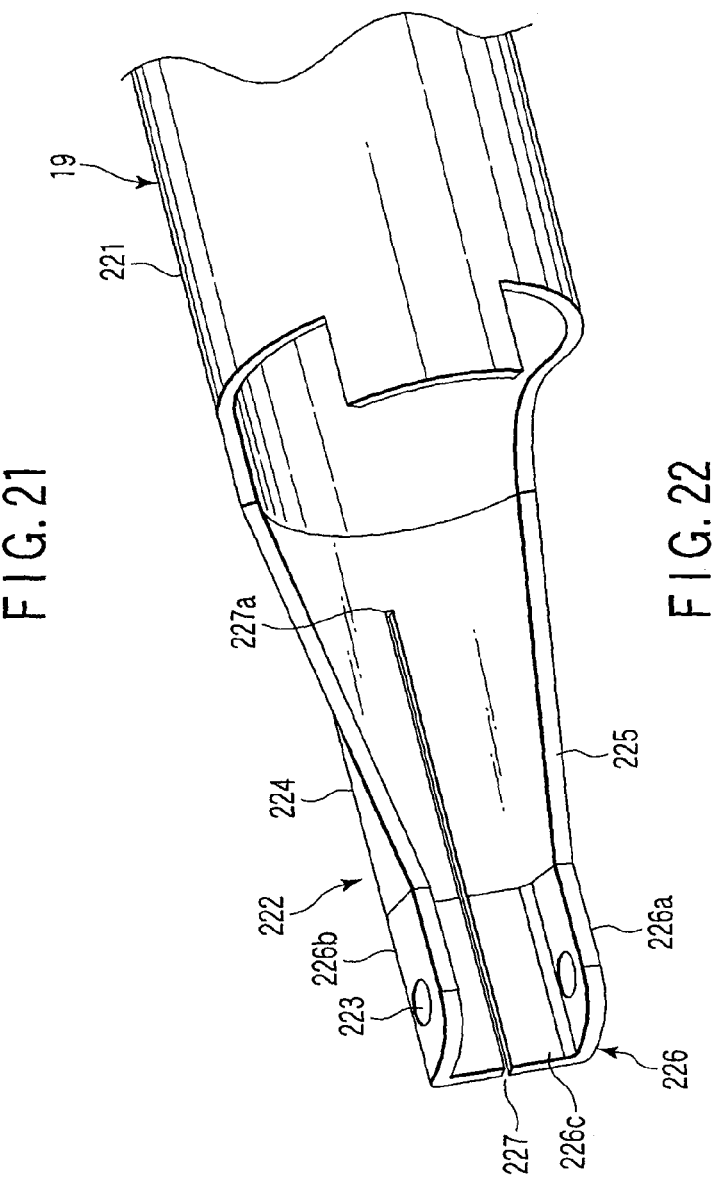
FIG. 22 is a perspective view showing a distal end portion of the driving pipe of the ultrasonic therapeutic apparatus according to the first embodiment.
Figure 23:
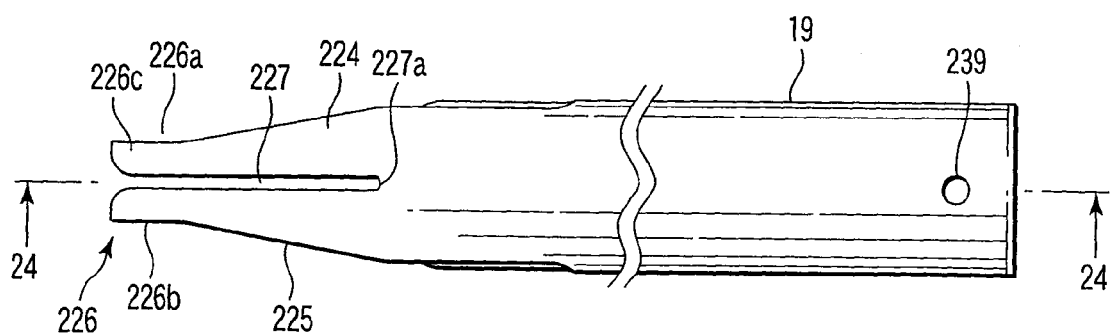
FIG. 23 is a plan view showing the driving pipe of the ultrasonic therapeutic apparatus according to the first embodiment.
Figure 24:
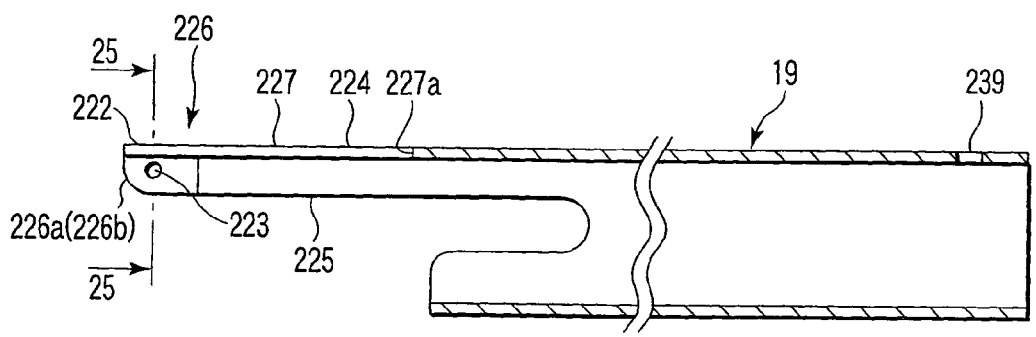
FIG. 24 is a cross-sectional view taken along line 24-24 in FIG. 23.
Figure 25:
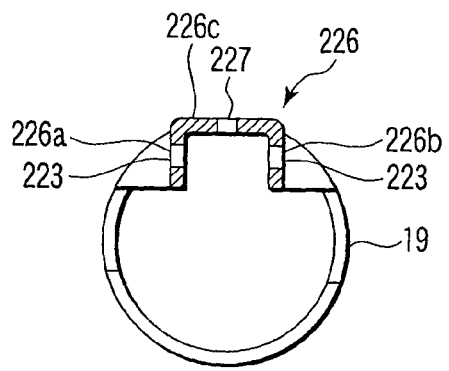
FIG. 25 is a front view showing the driving pipe of the ultrasonic therapeutic apparatus according to the first embodiment.

As shown in FIG. 22, the peripheral wall of a tubular distal end portion of the body section 221 includes a crescent-shaped arcuate cross-sectional portion 224, which is formed by leaving a substantially crescent-shaped arcuate cross-sectional portion over a predetermined length in the axial direction, and cutting out the other portion. As shown in FIG. 23, the arcuate cross-sectional portion 224 includes a taper portion 225 with a tapered distal end portion, which is gradually tapered toward the distal end side. As shown in FIG. 22 and FIG. 25, a U-shaped portion 226 having a U-shaped cross section is formed at a distal end of the taper portion 225. The operating section 222 is constituted by the U-shaped portion 226.

As shown in FIG. 22, the U-shaped portion 226 has two side surfaces 226a and 226b, which are opposed to each other, and a connecting surface 226c which connects the two side surfaces 226a and 226b. The connection section 223 is formed in each of the two side surfaces 226a and 226b of the U-shaped portion 226.

The operating section 222 has a slit 227 extending in the axial direction of the sheath 18 in a distal end portion of the connecting surface 226c. As shown in FIG. 23, the slit 227 has a terminal end portion 227a which is located at a position corresponding to a proximal end portion of the taper portion 225.

As shown in FIG. 8A, the insulation tube 24 includes a projection portion 228 which projects forward of the body section 221 of the driving pipe 19. The projection portion 228 extends up to a rear end position of the U-shaped portion 226.

Further, a proximal end portion of the insulation tube 24 extends to a proximal end side of the sheath body 16. The driving pipe 19 and probe unit 3 are electrically insulated by the insulation tube 24.

FIG. 9 shows a proximal end portion of the sheath body 16. The proximal end portion of the sheath 18 includes a flare portion 229 which has a greater inside diameter than the other portion. A proximal end portion of the driving pipe 19 extends more rearward than the flare portion 229 of the sheath 18.

Seal means 230 for effecting sealing between the sheath 18 and the driving pipe 19 is provided between the flare portion 229 and the driving pipe 19. The seal means 230 includes two backup rings 231 and 232 and one O ring 233. The two backup rings 231 and 232 are disposed between the flare portion 229 and the driving pipe 19 in the state in which the two backup rings 231 and 232 are paired in a back-and-forth direction along the axis of the sheath 18. The O ring 233 is provided between the backup rings 231 and 232 so as to be movable in the axial direction of the sheath 18.

In addition, the proximal end portion of the sheath body 16 is provided with an attachment/detachment mechanism section 31 for attachment/detachment to/from the handle unit 4. The attachment/detachment mechanism section 31 includes a cylindrical large-diameter handle member 32 which is formed of a resin material, a guide cylindrical body (first tubular member) 33 which is formed of a metallic cylindrical body, and a cylindrical connection tube body (second tubular member) 34 which is formed of a resin material.

The guide cylindrical body 33 includes a tubular body 33a which is fitted on the flare portion 229 of the proximal end portion of the sheath 18 and extends rearward. A distal end portion of the tubular body 33a is provided with a large-diameter 33b which has a greater outside diameter than the other portion thereof. The handle member 32 is fitted on the large-diameter portion 33b. A connection flange portion 33c, which projects outward, is formed on an outer peripheral surface of a rear end portion of the guide cylindrical body 33.

Figure 27:
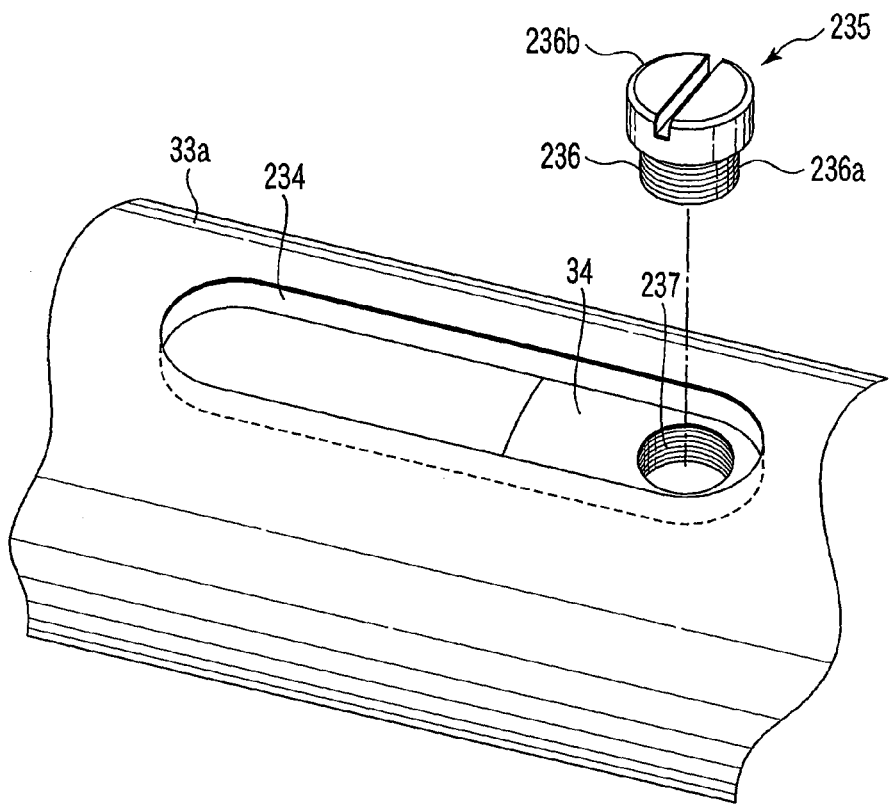
FIG. 27 is a perspective view showing the state before the threaded pin is engaged in the assembly section at the proximal end portion of the sheath unit of the ultrasonic therapeutic apparatus according to the first embodiment.

As shown in FIG. 27, an outer peripheral wall portion of the tubular 33a has an elongated slit 234 extending in the axial direction of the sheath 18. In addition, on the rear end portion side of the guide cylindrical body 33, a distal end portion of the connection tube body 34 is inserted so as to be slidable in the axial direction of the sheath 18. A proximal end portion of the driving pipe 19 is fitted and inserted inside the inner peripheral surface of the distal end portion of the connection tube body 34.

Figure 26:
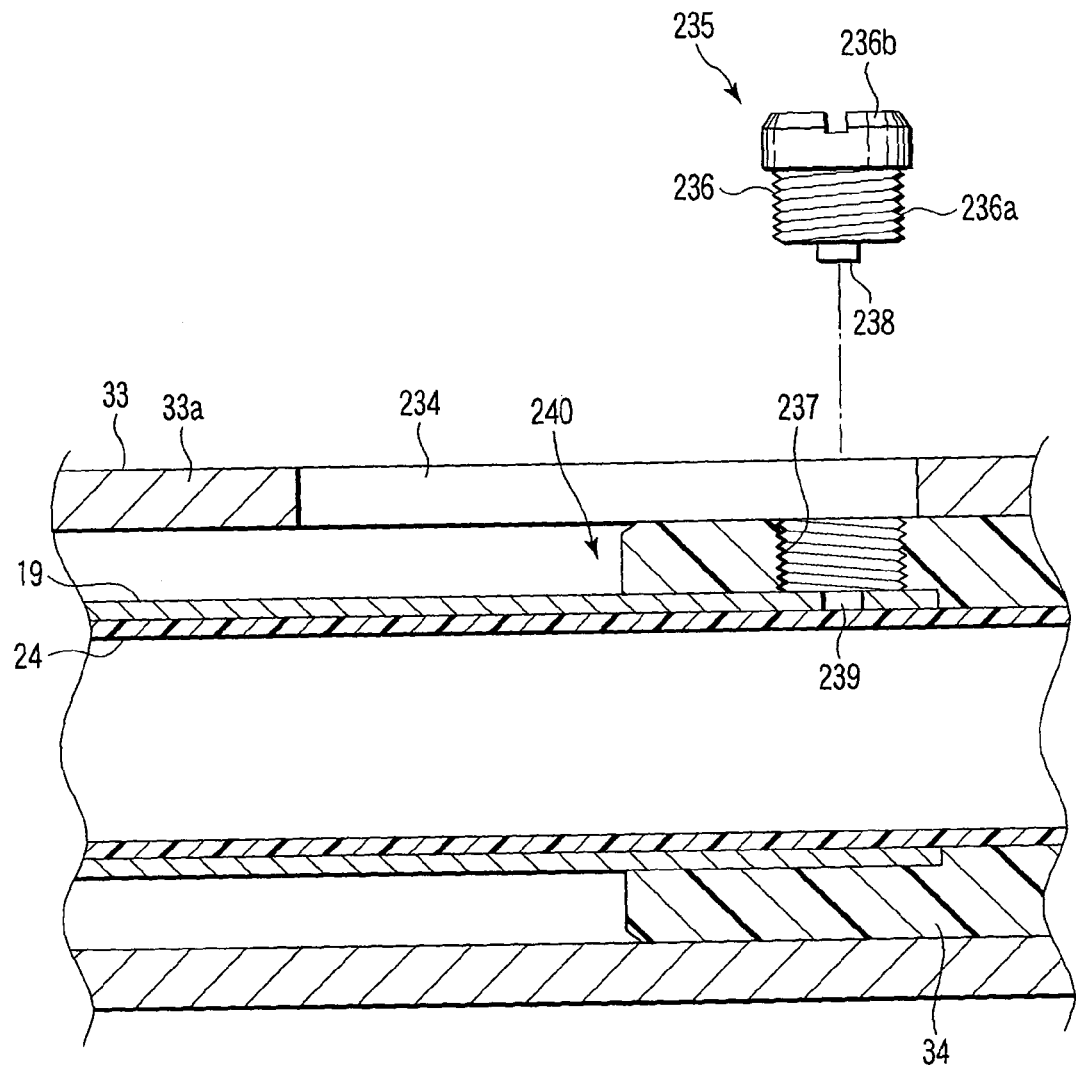
FIG. 26 is a longitudinal cross-sectional view showing a state before a threaded pin is engaged in an assembly section at the proximal end portion of the sheath unit of the ultrasonic therapeutic apparatus according to the first embodiment.
Figure 28:
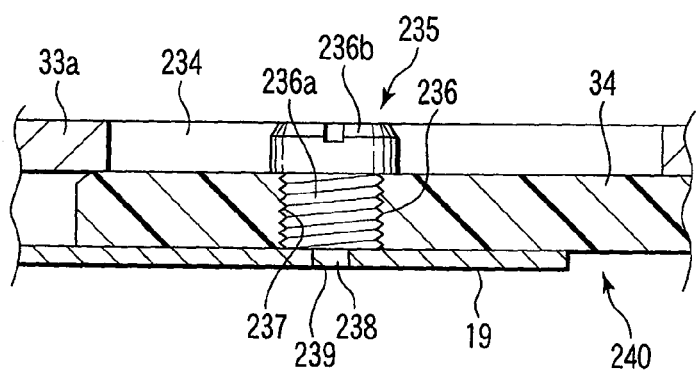
FIG. 28 is a longitudinal cross-sectional view showing the state in which the threaded pin is engaged in the assembly section at the proximal end portion of the sheath unit of the ultrasonic therapeutic apparatus according to the first embodiment.

As shown in FIG. 28, a threaded pin (projection body) 235 is fixed to a proximal end portion of the driving pipe 19. As shown in FIG. 26, the threaded pin 235 includes a male screw member 236. A threaded hole portion 237, which is engaged with a male screw portion 236a of the threaded pin 235, is formed in the connection tube body 34.

A large-diameter portion 236b, which has a greater diameter than the male screw portion 236a, is formed on a head portion of the screw member 236. The large-diameter portion 236b of the threaded pin 235 is an engaging portion which is engaged in the slit 234 of the guide cylindrical body 33.

A small-diameter portion 238, which has a smaller diameter than the male screw portion 236a, is provided on the threaded pin 235 so as to project on a side opposite to the head portion of the screw member 236. The small-diameter portion 238 is inserted and fitted in a fixing hole 239 which is formed in a proximal end portion of the driving pipe 19. Thereby, the male screw portion 236a of the threaded pin 235 is engaged in and passed through the screw hole portion 237 of the connection tube body 34, and a coupling body 240, in which the driving pipe 19 and the connection tubular body 34 are coupled, is formed. Further, the large-diameter portion 236b of the threaded pin 235 is engaged with the slit 234 of the guide cylindrical body 33, and thereby the coupling body 240 is coupled to the guide cylindrical body 33 so as to be movable as one body along the slit 234 in the axial direction of the sheath 18.

A fixing section 35 of the guide cylindrical body 33 is formed by an engaging section between the handle member 32 and the large-diameter portion 33b of the guide cylindrical body 33. Further, in the handle member 32, an attachment/detachment section 36 for attachment/detachment to/from the handle unit 4 is disposed on the rear side of the fixing section 35.

Figure 29:
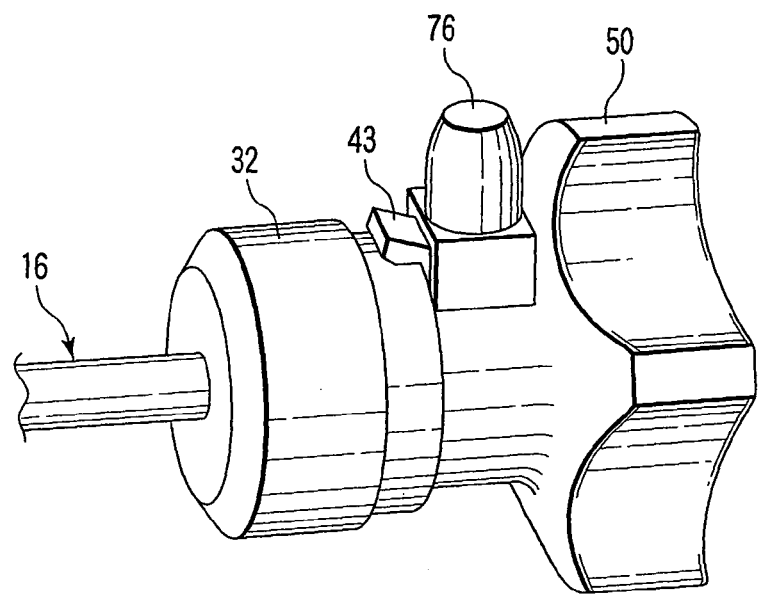
FIG. 29 is a perspective view showing a state prior to rotational engagement at the time when the handle unit and sheath unit of the ultrasonic therapeutic apparatus according to the first embodiment are coupled.
Figure 30:
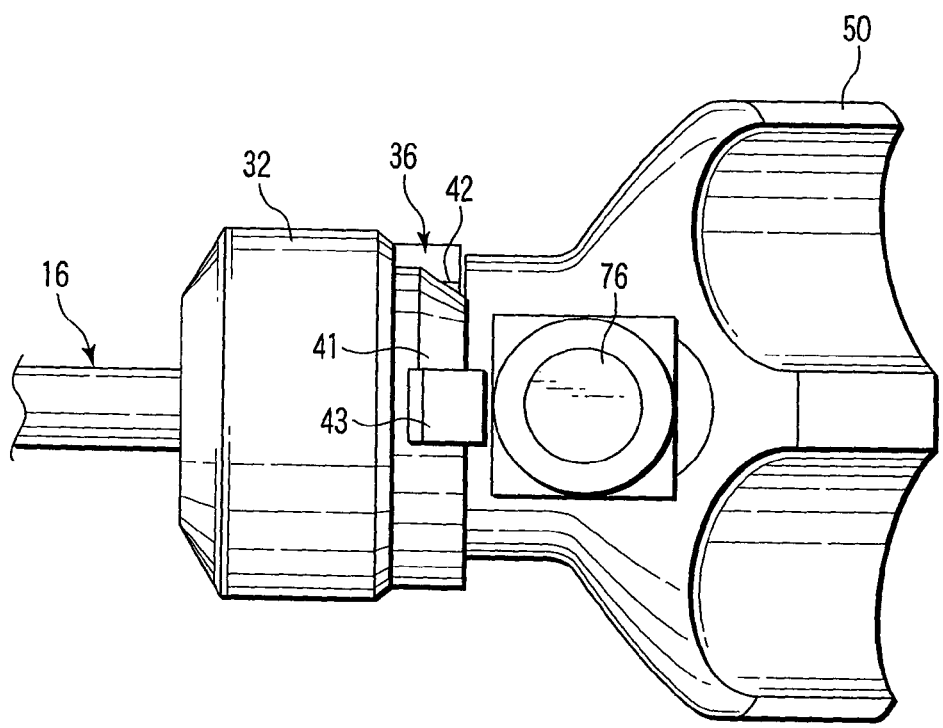
FIG. 30 is a plan view showing the state prior to rotational engagement at the time when the handle unit and sheath unit of the ultrasonic therapeutic apparatus according to the first embodiment are coupled.
Figure 31:
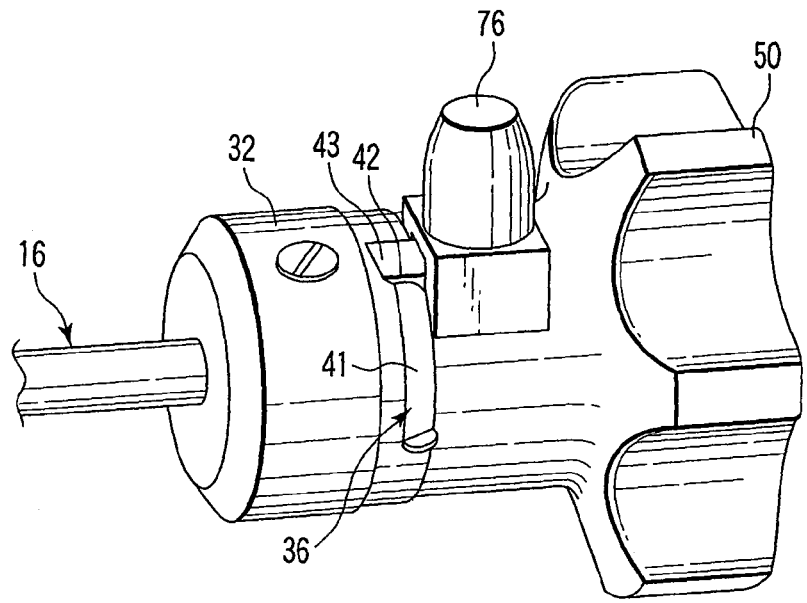
FIG. 31 is a perspective view showing a state after the rotational engagement at the time when the handle unit and sheath unit of the ultrasonic therapeutic apparatus according to the first embodiment are coupled.
Figure 32:
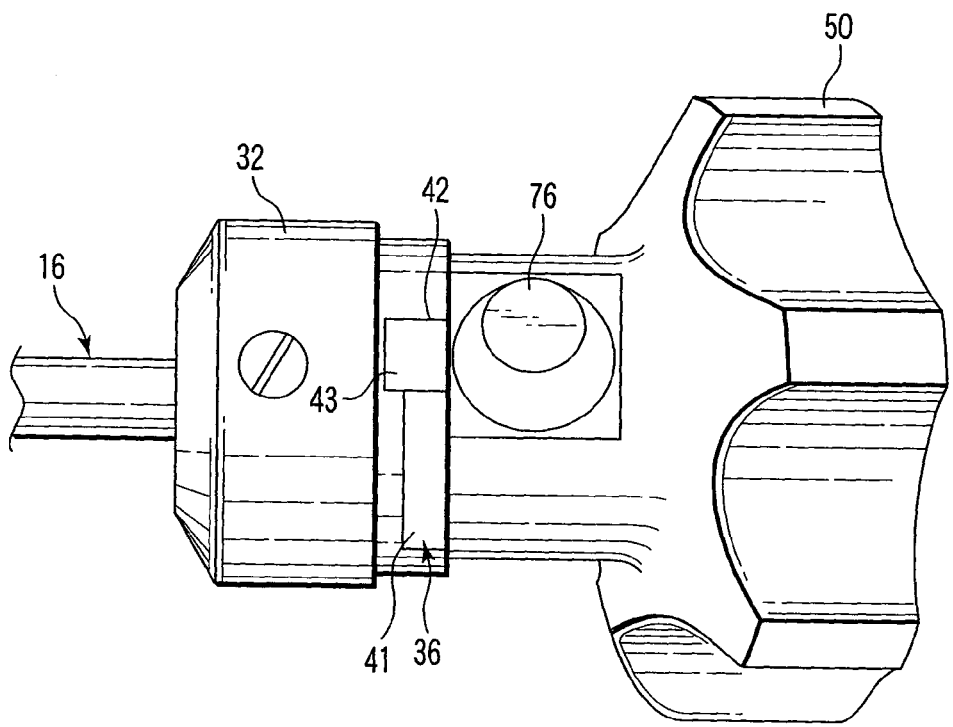
FIG. 32 is a plan view showing the state after the rotational engagement at the time when the handle unit and sheath unit of the ultrasonic therapeutic apparatus according to the first embodiment are coupled.

FIG. 29 to FIG. 32 show the structure of the attachment/detachment part between the handle member 32 and the handle unit 4. As shown in FIGS. 30 to 32, the attachment/detachment section 36 of the handle member 32 has a guide groove 41 with an inclined surface, and an engaging recess portion 42. The guide groove 41 is provided to extend in a circumferential direction on the outer peripheral surface of the proximal end portion of the handle member 32. In addition, the guide groove 41 has a tapered inclined surface with an outside diameter decreasing toward the rear end portion side of the handle member 32.

Figure 33:
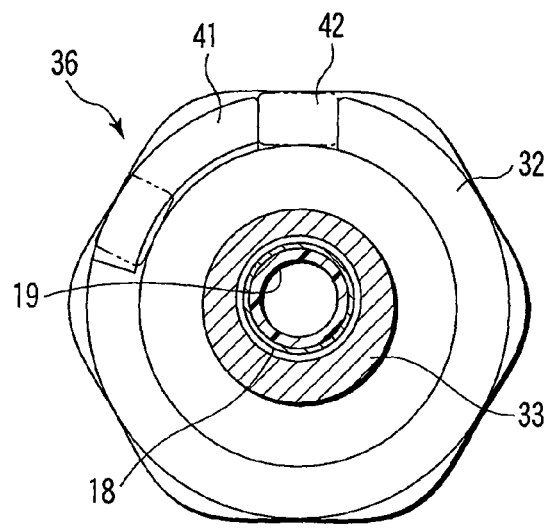
FIG. 33 is an explanatory view for explaining a positional relationship between a guide groove and an engaging recess portion at the coupling section between the handle unit and sheath unit of the ultrasonic therapeutic apparatus according to the first embodiment.

As shown in FIG. 33, the engaging recess portion 42 is formed at one end portion of the guide groove 41. The engaging recess portion 42 is formed of a recess portion having a smaller diameter than the inclined surface of the guide groove 41. The engaging recess portion 42 is configured such that the engaging lever 43 (to be described later) on the handle unit 4 side is disengageably engaged in the engaging recess portion 42. FIGS. 31 and 32 show the state in which the engaging lever 43 is engaged in the engaging recess portion 42, and FIGS. 29 and 30 show the disengaged state in which the engaging lever 43 is pulled out of the engaging recess portion 42.

Figure 34:
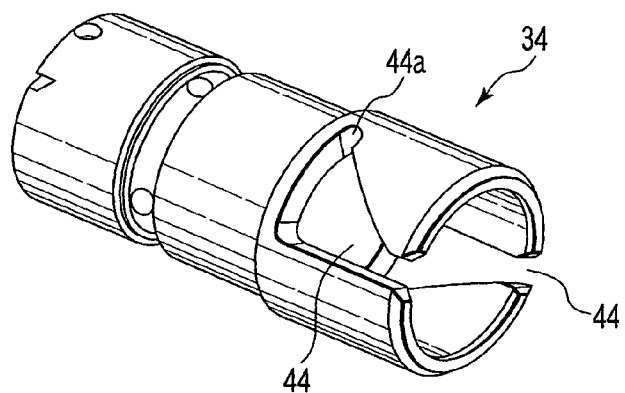
FIG. 34 is a perspective view showing a connection tube body of the sheath unit of the ultrasonic therapeutic apparatus according to the first embodiment.
Figure 35:
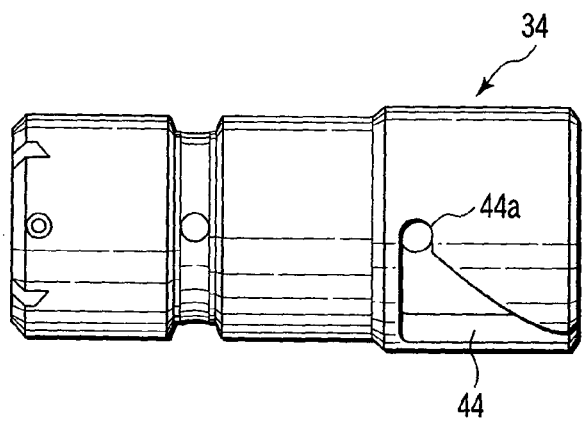
FIG. 35 is a perspective view showing the connection tube body of the sheath unit of the ultrasonic therapeutic apparatus according to the first embodiment.

As shown in FIGS. 34 and 35, a proximal end portion of the connection tube body 34 has two guide grooves 44 which are used at a time of attachment/detachment to/from the handle unit 4 side. The guide grooves 44 are configured such that two engaging pins 45 (to be described later) on the handle unit 4 side are disengageably engaged in the guide grooves 44, respectively. An engaging groove 44a, which restricts movement of the engaging pin 45 in the axial direction of the sheath body 16, is formed at a terminal end portion of the guide groove 44.

Figure 9B:
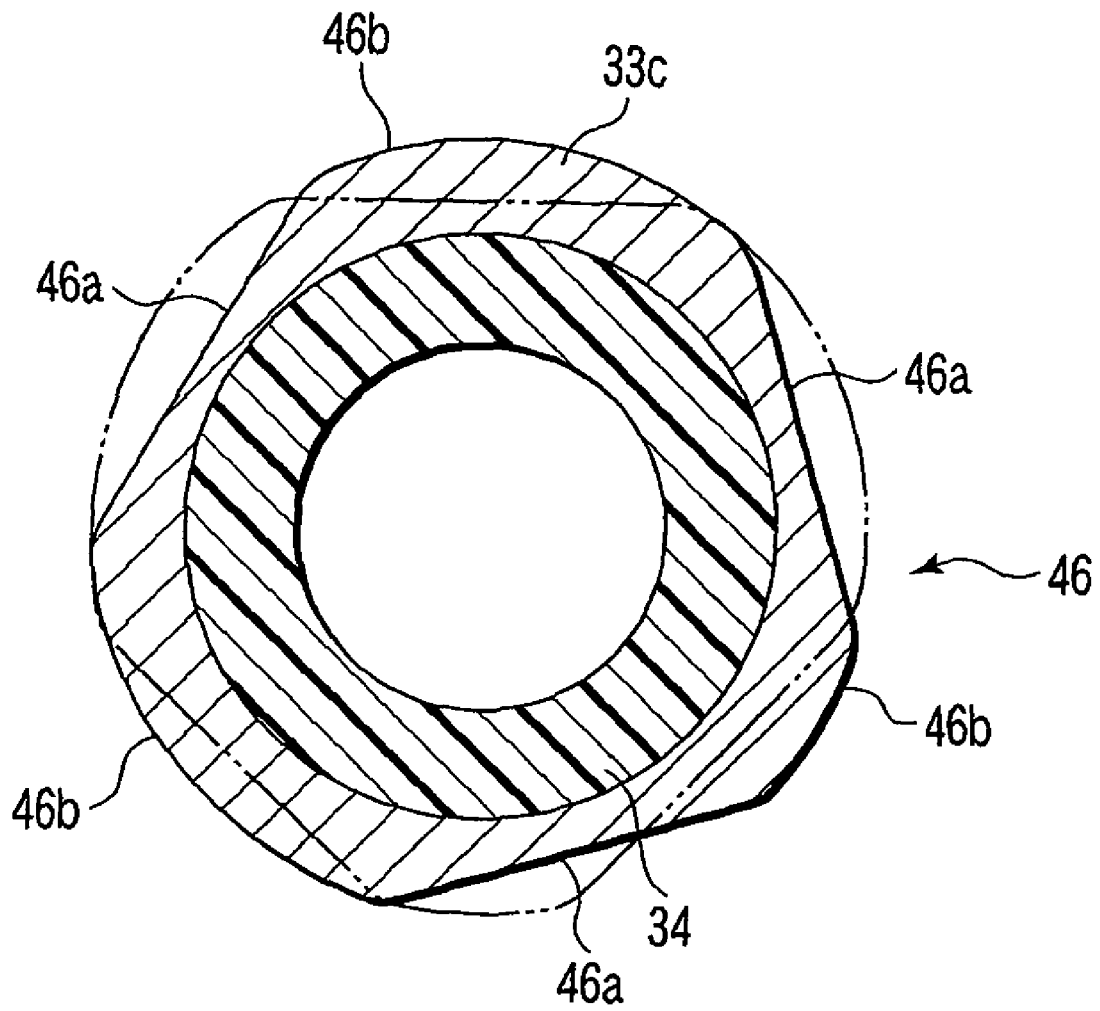
FIG. 9B is a cross-sectional view taken along line IXB-IXB in FIG. 9A.

As shown in FIG. 9B, the connection flange portion 33c of the guide cylindrical body 33 has a non-circular engaging portion 46. The engaging portion 46 has three cut-out flat-surface portions 46a at a plurality of locations on the circular outer peripheral surface of the connection flange portion 33c, for example, at three locations in this embodiment. Corner portions 46b, each having a greater diameter than the flat-surface portion 46a, are formed at connection parts between the three flat-surface portions 46. Thereby, the engaging portion 46 with a substantially triangular cross section is formed on the connection flange portion 33c. It is not necessary that the non-circular engaging portion 46 have a substantially triangular shape. The non-circular engaging portion 46 may have any other non-circular shape, for instance, a polygon such as a rectangle or a pentagon.

Figure 3:
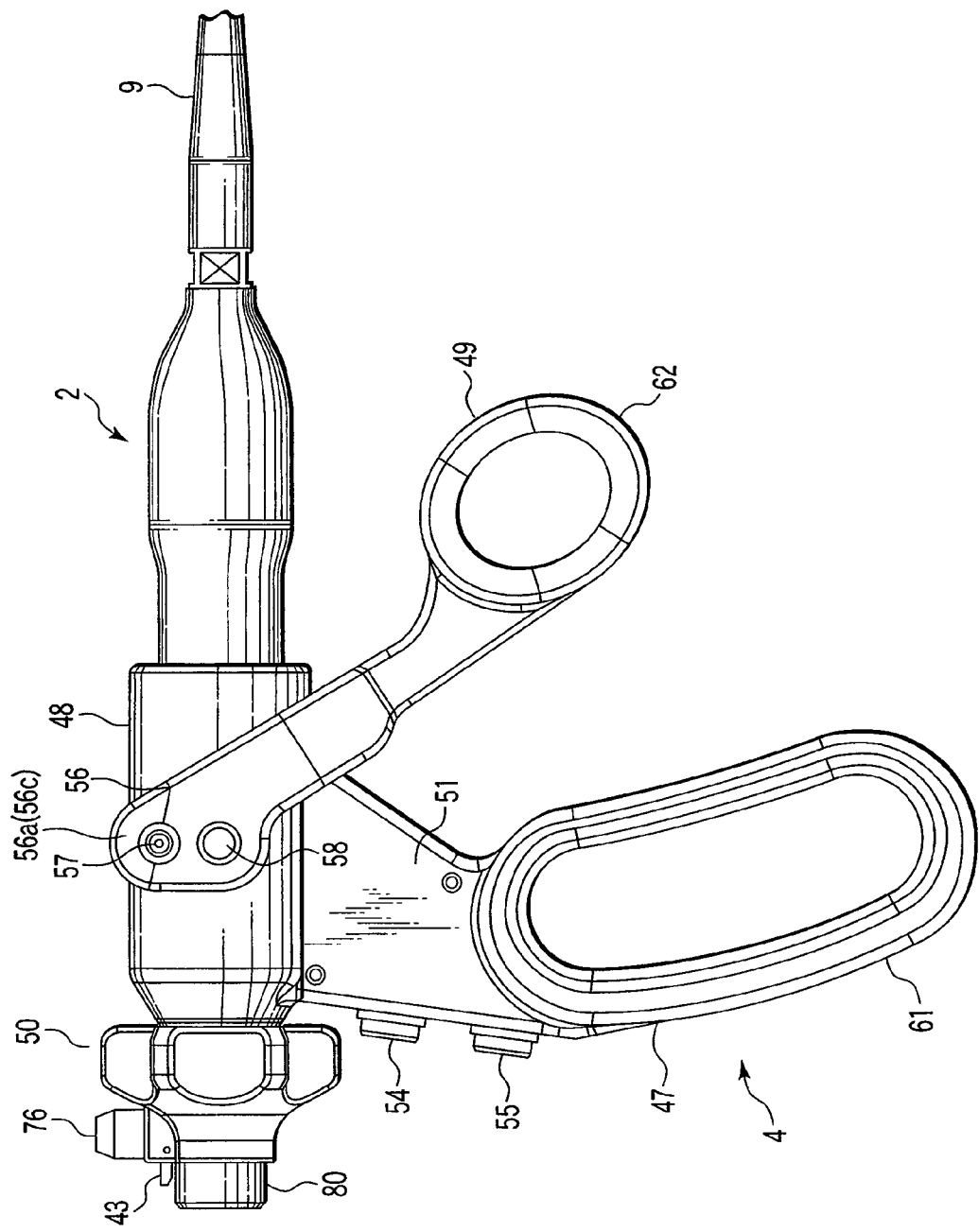
FIG. 3 is a side view showing a coupled state between a handle unit and a transducer unit of the ultrasonic therapeutic apparatus according to the first embodiment.
Figure 36:
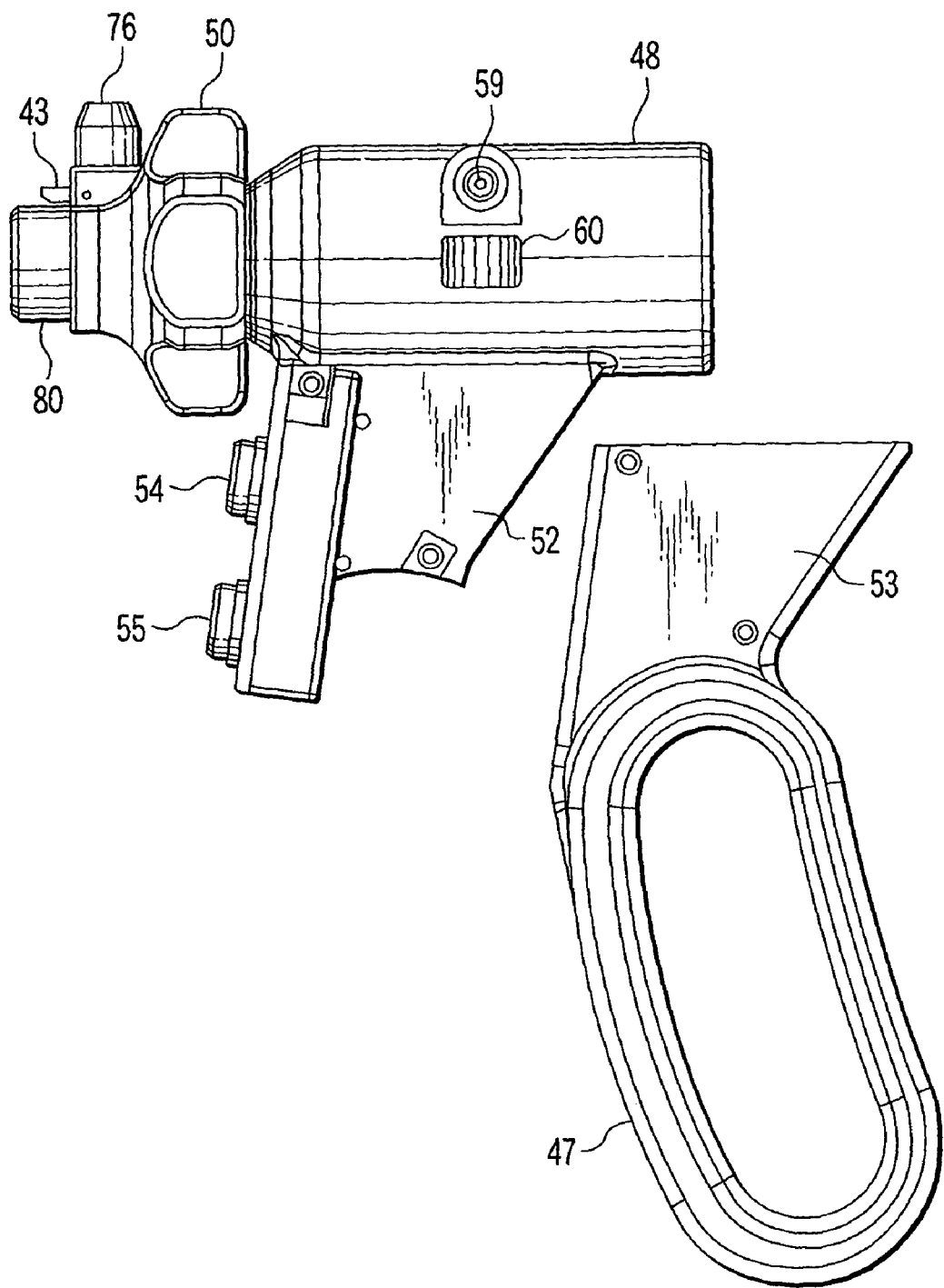
FIG. 36 is a side view showing a state before an attachment member is attached to a base member of a stationary handle of the handle unit of the ultrasonic therapeutic apparatus according to the first embodiment.

As shown in FIG. 3, the handle unit 4 mainly includes a stationary handle 47, a hold cylinder 48, a movable handle 49 and a rotational operation knob 50. The hold cylinder 48 is provided on the upper part of the stationary handle 47. A switch hold section 51 is provided between the stationary handle 47 and the hold cylinder 48. As shown in FIG. 36, the switch hold section 51 includes a switch attachment section 52 which is fixed to a lower end portion of the hold cylinder 48, and a cover member 53 which is fixed to an upper end portion of the stationary handle 47.

Figure 37:
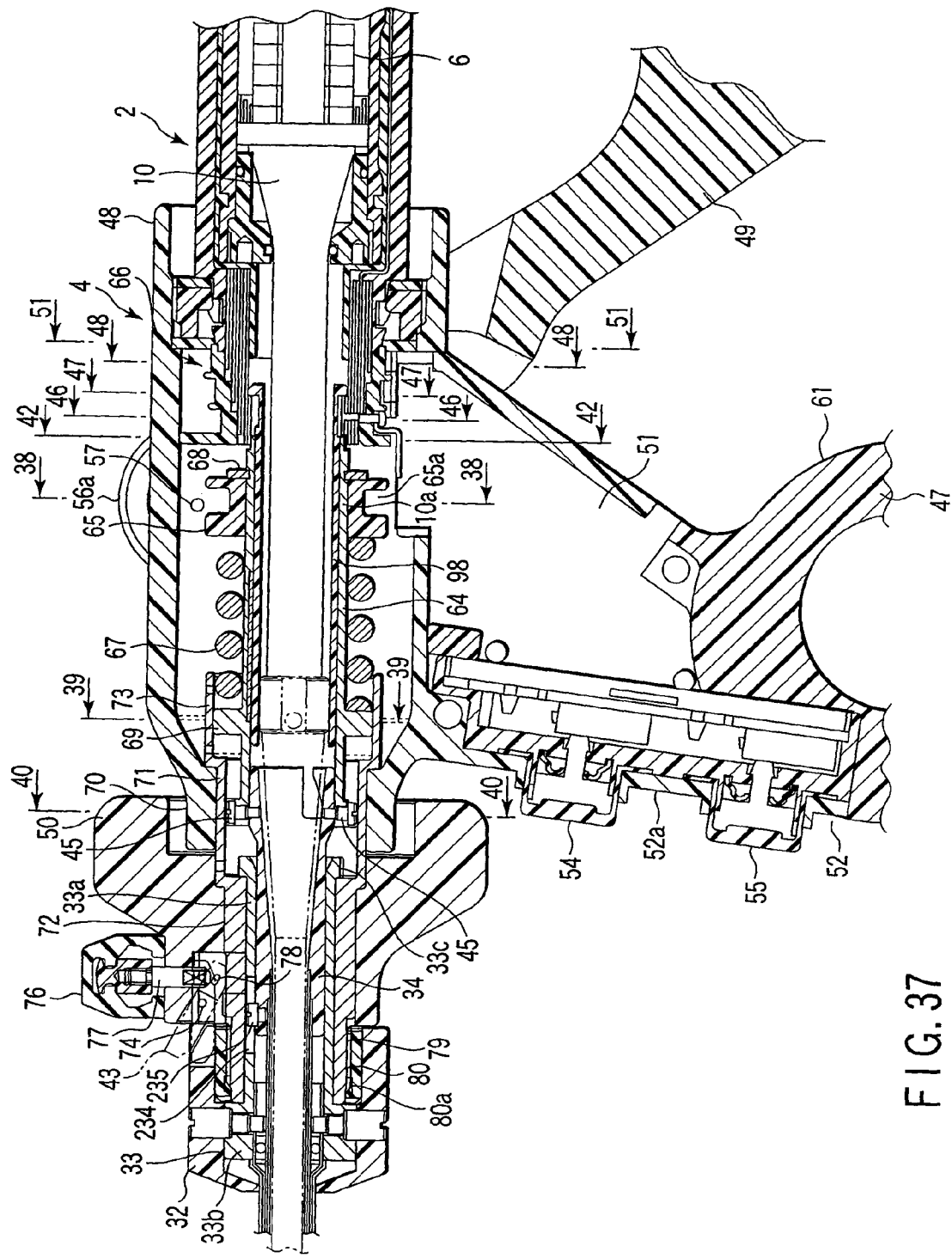
FIG. 37 is a longitudinal cross-sectional view showing a state after engagement between the handle unit and sheath unit of the ultrasonic therapeutic apparatus according to the first embodiment.

As shown in FIG. 37, the switch attachment section 52 has a switch attachment surface 52a on a front side thereof, to which a plurality of hand switches, for example, two hand switches (first switch 54 and second switch 55) in the present embodiment, are attached. The first switch 54 and second switch 55 are switches for selecting therapeutic functions of the therapeutic section 1A of the handpiece 1.

In the switch attachment section 52, the first switch 54 and second switch 55 are arranged in the up-and-down direction. The first switch 54 is disposed on an upper side of the switch attachment surface 52a, and is set to be a switch which selects a first therapeutic function that is frequently used among the plural therapeutic functions. The second switch 55 is disposed on a lower side of the switch attachment surface 52a, and is set to be a switch which selects another second therapeutic function of the plural therapeutic functions.

As shown in FIG. 2, the movable handle 49 has a substantially U-shaped arm section 56 at an upper part thereof. The U-shaped arm section 56 includes two arms 56a and 56b. The movable handle 49 is assembled to the hold cylinder 48 in the state in which the hold cylinder 48 is inserted between the two arms 56a and 56b.

Each of the arms 56a and 56b has a support pin 57 and an operation pin 58. As shown in FIG. 36, a pin receiving hole portion 59 and a window portion 60 are formed in each of both side portions of the hold cylinder 48. The support pin 57 of each arm 56a, 56b is inserted in the pin receiving hole portion 59 of the hold cylinder 48. Thereby, an upper end portion of the movable handle 49 is rotatably supported on the hold cylinder 48 via the support pins 57.

Ring-shaped finger hook portions 61 and 62 are provided on lower end portions of the stationary handle 47 and movable handle 49, respectively. By hooking the fingers on the finger hook portions 61 and 62 and holding them, the movable handle 49 rotates via the support pins 57 and the movable handle 49 is opened/closed relative to the stationary handle 47.

The operation pins 58 of the movable handle 49 extend into the hold cylinder 48 through the window portions 60 of the hold cylinder 48. An operation force transmission mechanism 63, which transmits an operation force of the movable handle 49 to the driving pipe 19 of the jaw 17, is provided inside the hold cylinder 48.

As shown in FIG. 37, the operation force transmission mechanism 63 mainly comprises a metallic cylindrical spring receiving member 64 and a resin-made slider member 65. The spring receiving member 64 is disposed coaxially with the center axis of the hold cylinder 48, and extends in the same direction as the direction of insertion of the probe unit 3.

A coil spring 67, the slider member 65, a stopper 68 and a spring receiver 69 are provided on an outer peripheral surface of the spring receiving member 64. A front end portion of the coil spring 67 is fixed to the spring receiver 69. The stopper 68 restricts the position of movement of a rear end side of the slider member 65. The coil spring 67 is disposed between the spring receiver 69 and the slider member 65 with a fixed amount of mounting force.

Figure 38:
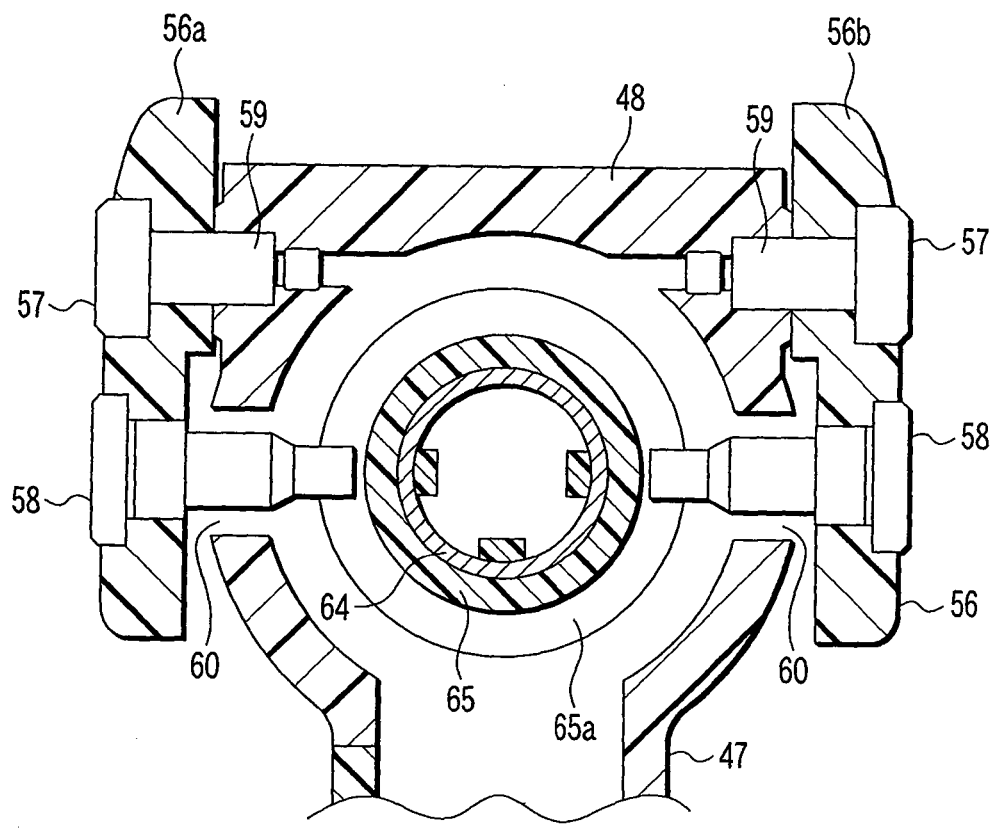
FIG. 38 is a cross-sectional view taken along line 38-38 in FIG. 37.
Figure 40:
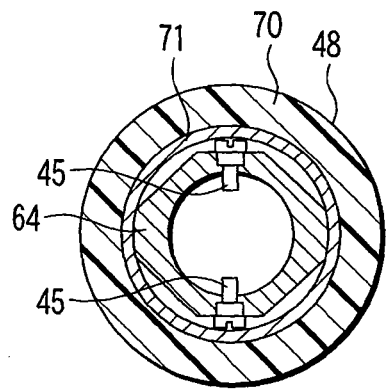
FIG. 40 is a cross-sectional view taken along line 40-40 in FIG. 37.

An annular engaging groove 65a is formed in a circumferential direction in an outer peripheral surface of the slider member 65. As shown in FIG. 38, the operation pins 58 of the movable handle 49 are inserted and engaged in the engaging groove 65a. If the movable handle 49 is held and the movable handle 49 is closed relative to the stationary handle 47, the operation pins 58 rotate about the support pins 57 in accordance with the rotational operation of the movable handle 49 at this time. The slider member 65, which is in interlock with the rotation of the support pins 57, moves forward in the axial direction. At this time, the spring receiving member 64, which is coupled to the slider member 65 via the coil spring 67, moves forward/backward together with the slider member 65. As shown in FIG. 40, a pair of engaging pins 45, which are used when the sheath unit 5 and the handle unit 4 are attached/detached, are fixed to a distal end portion of the spring receiving member 64. Thereby, the operation force of the movable handle 49 is transmitted to the connection tube body 34 of the sheath unit 5 via the pair of engaging pins 45, and the driving pipe 19 of the jaw 17 moves forward. Thereby, the jaw body 201 of the jaw 17 rotates via the support pin 27.

Further, when a living body tissue is clamped between the hold member 202 of the jaw 17 and the probe distal end portion 3a of the probe unit 3 by this operation, the hold member 202 rotates over a certain angle about the pin 214 in accordance with the bending of the probe distal end portion 3a so that force uniformly acts over the entire length of the hold member 202. In this state, ultrasonic is output and a living body tissue, such as a blood vessel, can be coagulated or cut.

An annular bearing portion 70 is formed at a front end portion of the hold cylinder 48. The bearing portion 70 is metallic, and a cylindrical rotation transmission member 71 is coupled to the bearing portion 70 rotatably about the axis. The rotation transmission member 71 includes a projecting portion 72 which projects forward of the bearing portion 70, and a large-diameter portion 73 which extends to the inner side of the hold cylinder 48 from the bearing portion 70.

The rotational operation knob 50 is fitted and fixed on the projecting portion 72. The engaging lever 43 is provided at the front end portion of the rotational operation knob 50. An intermediate portion of the engaging lever 43 is rotatably coupled to the projecting portion 72 via a pin 74. A proximal end portion of the engaging lever 43 extends to the inside of a lever receiving recess portion 75 which is formed in a front surface of the rotational operation knob 50.

An operation button 76 for operating the engaging lever 43 in such a direction as to disengage the engaging lever 43 is provided on an outer peripheral surface of the front end portion of the rotational operation knob 50. An operation pin 77, which is disposed downward, is provided so as to project from the operation button 76. The operation pin 77 extends to the inside of the lever receiving recess portion 75 through a wall hole of the rotational operation knob 50. A proximal end portion of the engaging lever 43 is rotatably coupled to a lower end portion of the operation pin 77 via a pin 78.

A removal prevention ring 80 for the rotational operation knob 50 is provided on a distal end portion of the projecting portion 72. A male threaded portion 79 is formed on the distal end portion of the projecting portion 72. A female threaded portion 80a, which is to be meshed with the male threaded portion 79, is formed on an inner peripheral surface of the removal prevention ring 80. The female threaded portion 80a of the removal prevention ring 80 is meshed and engaged with the male threaded portion 79 of the projecting portion 72, and thereby the rotational operation knob 50 is fixed to the rotation transmission member 71.

Figure 39:
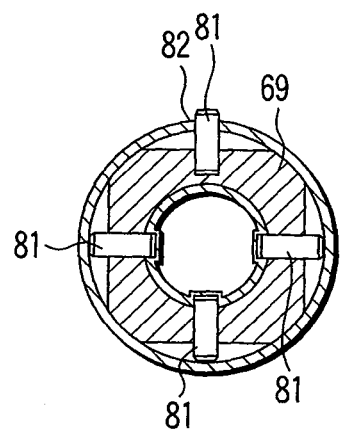
FIG. 39 is a cross-sectional view taken along line 39-39 in FIG. 37.

As shown in FIG. 39, the spring receiver 69 of the spring receiving member 64 is provided with four metallic positioning pins 81 which project radially outward. An elongated engaging hole portion 82, in which one pin 81 of the spring receiving member 64 is inserted, is formed in the large-diameter portion 73 of the rotation transmission member 71. The engaging hole portion 82 extends in the same direction as the direction of insertion of the probe unit 3. Thereby, when the movable handle 49 is operated, the pin 81 is moved along the engaging hole portion 82 and thus the advancing/retreating movement of the spring receiving member 64 is prevented from being transmitted to the rotation transmission member 71.

On the other hand, when the rotational operation knob 50 is rotated, the rotational movement of the rotation transmission member 71, which rotates together with the rotational operation knob 50, is transmitted to the spring receiving member 64 via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob as one body about the axis thereof.

Figure 41B:
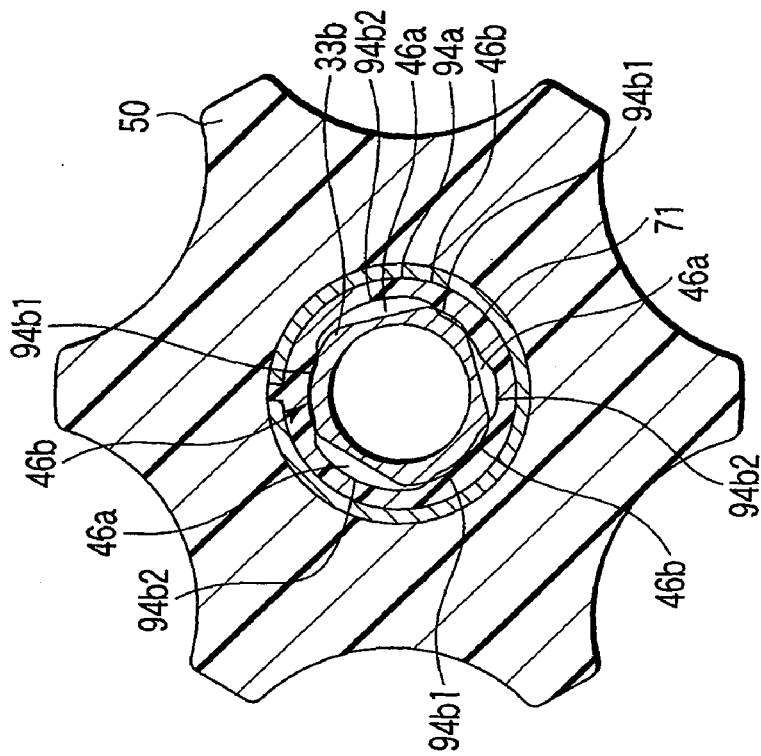
FIG. 41B is a vertical cross-sectional view showing a state prior to engagement of the engagement section between the handle unit and sheath unit of the ultrasonic therapeutic apparatus according to the first embodiment.
Figure 41A:
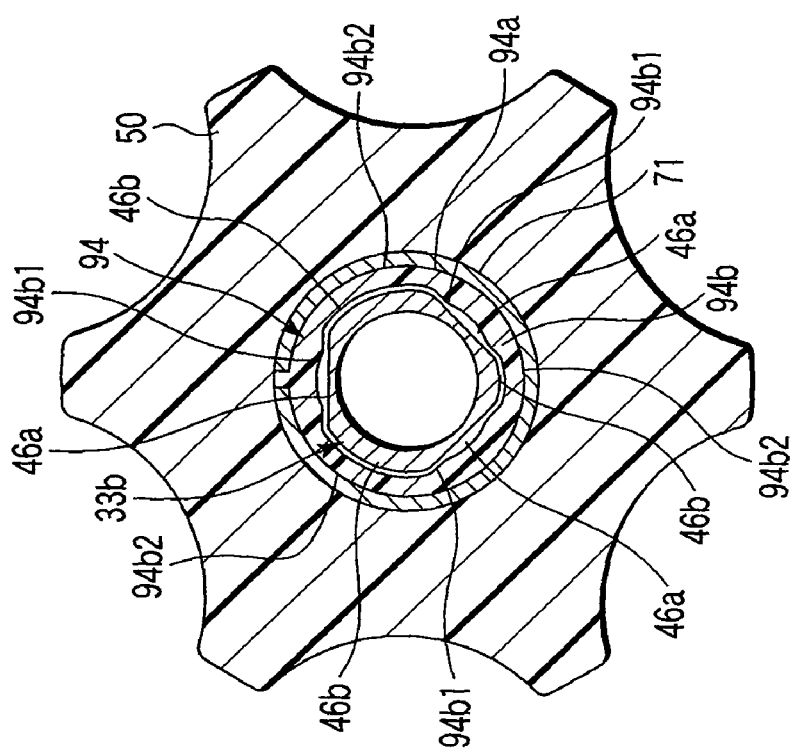
FIG. 41A is a vertical cross-sectional view showing a state prior to engagement of the engagement section between the handle unit and sheath unit of the ultrasonic therapeutic apparatus according to the first embodiment.

Engaging means 94, which is disengageably engaged with the connection flange portion 33c of the sheath unit 5, is provided on the inner peripheral surface of the rotation transmission member 71. FIGS. 41A and 41B show the engaging means 94. The engaging means 94 includes an insertion hole portion 94a in which the connection flange portion 33c is inserted when the sheath unit 5 and handle unit 4 are coupled, and an electrically conductive rubber ring (urging means) 94b which is disposed within the insertion hole portion 94a.

The shape of the inner peripheral surface of the electrically conductive rubber ring 94b is substantially the same as the shape of the engaging portion 46 of the connection flange portion 33c. Specifically, the inner peripheral surface of the electrically conductive rubber ring 94b has three cut-out flat-surface portions 94b1 at a plurality of locations on the circular outer peripheral surface, for example, at three locations in this embodiment, and three corner portions 94b2 which are located at connection parts between the three flat-surface portions 94b1 and have greater diameters than the flat-surface portions 94*b*1. Thereby, the electrically conductive rubber ring 94*b* has a substantially triangular cross-sectional shape. Thus, as shown in FIG. 41A, the electrically conductive rubber ring 94*b* is held in a natural, non-compressed position in the positional state in which the inner peripheral surface shape of the electrically conductive rubber ring 94*b* corresponds to the engaging portion 46 of the connection flange portion 33*c*, that is, in the state in which the three corner portions 46*b* of the connection flange portion 33*c* correspond in position to the three corner portions 94*b*2 of the electrically conductive rubber ring 94*b*. On the other hand, by rotating the handle unit 4 and the sheath unit 5 relative to each other about the center axis of the sheath unit 5, the position of the electrically conductive rubber ring 94*b* is switched to a pressure contact position, as shown in FIG. 41B, where the electrically conductive rubber ring 94*b* is pressed on the three corner portions 46*b* of the connection flange portion 33*c*. At this time, the three corner portions 46*b* of the connection flange portion 33*c* are put in contact with, and pressed by, the three flat-surface portions 94*b*1 of the electrically conductive rubber ring 94*b*.

In the present embodiment, at the time of coupling the sheath unit 5 and handle unit 4, when the connection flange portion 33*c* of the sheath unit 5 is inserted straight into the electrically conductive rubber ring 94*b* (see FIG. 29 and FIG. 30), the electrically rubber ring 94*b* is held in the natural, non-compressed position, as shown in FIG. 41A. At this time, the engaging lever 43 on the handle unit 4 side is held in the state in which the engaging lever 43 rests on the inclined surface of the guide groove 41 of the handle member 32 of the sheath unit 5. Subsequently, the handle member 32 of the sheath unit 5 is rotated about the axis, relative to the handle unit 4. Thereby, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94*b* is switched to the pressure contact position where the electrically conductive rubber ring 94*b* is put in pressure contact with the three corner portions 46*b* of the connection flange portion 33*c*. Thereby, a sheath-unit-side electric path 40 (formed between the guide cylindrical body 33, fixing screw 39, coupling pipe 38, sheath 18, distal end cover 25, support pin 27 and jaw body 28) and a handle-unit-side electric path 95 (formed between an electrical contact member 96, spring receiving member 64, positioning pin 81 and rotation transmission member 71) are electrically connected via the electrically conductive rubber ring 94*b*. In this case, a second high-frequency electric path 97, which transmits a high-frequency current, is formed in the coupled body of the sheath unit 5 and handle unit 4.

Figure 42:
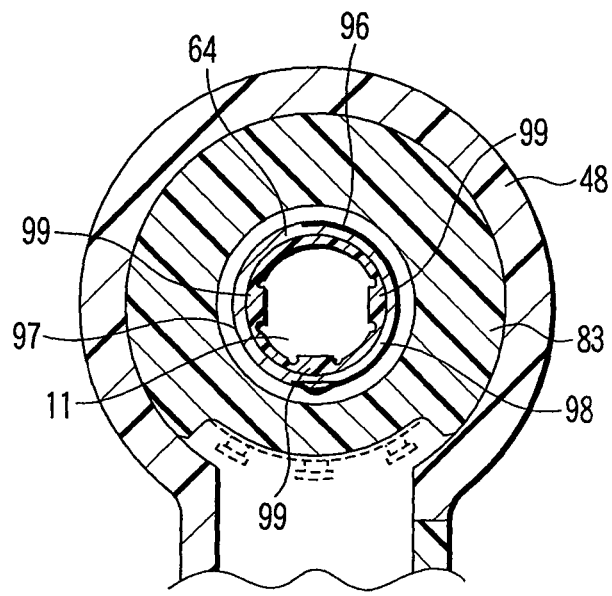
FIG. 42 is a cross-sectional view taken along line 42-42 in FIG. 37.

As shown in FIG. 42, the handle unit 4 includes a tubular member 98 which is formed of an insulating material on the inner peripheral surface of the spring receiving member 64. The tubular member 98 is fixed on the inner peripheral surface of the spring receiving member 64. Thereby, when the probe unit 3 and the handle unit 4 are connected, the first high-frequency electric path 13 and the second high-frequency electric path 97 are insulated by the tubular member 98.

An inner peripheral surface of the tubular member 98 has three engaging projection portions 99 which correspond to the three engaging recess portions 15 (see FIG. 6) of the flange portion 14 of the probe unit 3. When the probe unit 3 and handle unit 4 are connected, the three engaging projection portions 99 of the tubular member 98 are disengageably engaged with the three engaging recess portions 15 of the flange portion 14 of the probe unit 3. Thereby, the rotational-directional position between the probe unit 3 and the tubular member 98 of the handle unit 4 is restricted. Hence, when the rotational operation knob 50 is rotated, the coupled body of the probe unit 3 and transducer unit 2 is rotated as one body together with the assembly unit within the hold cylinder 48.

The engaging section between the flange portion 14 of the probe unit 3 and the tubular member 98 is not limited to the above-described structure. For example, the tubular member 98 may be formed to have a D-shaped cross section, and the flange portion 14 of the probe unit 3 may be formed to have a corresponding D-shaped cross section.

Figure 43:
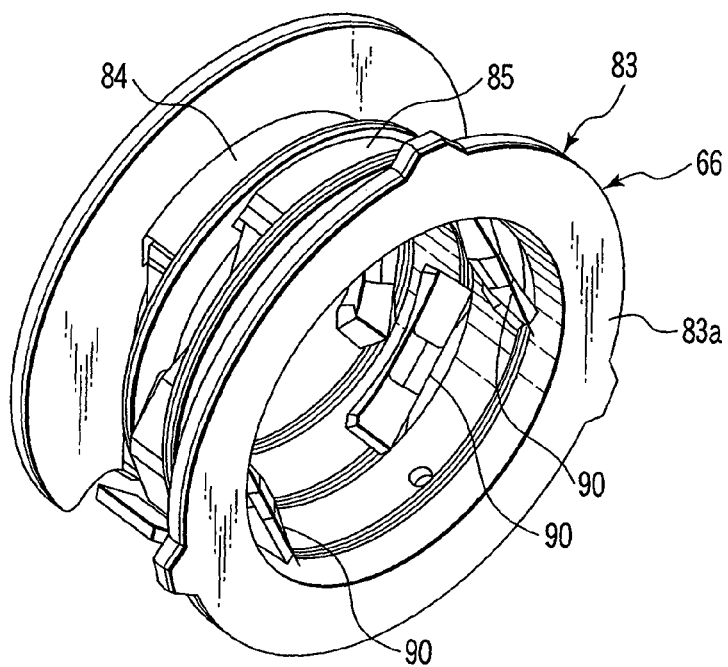
FIG. 43 is a perspective view showing an electrode hold member of the ultrasonic therapeutic apparatus according to the first embodiment.
Figure 44:
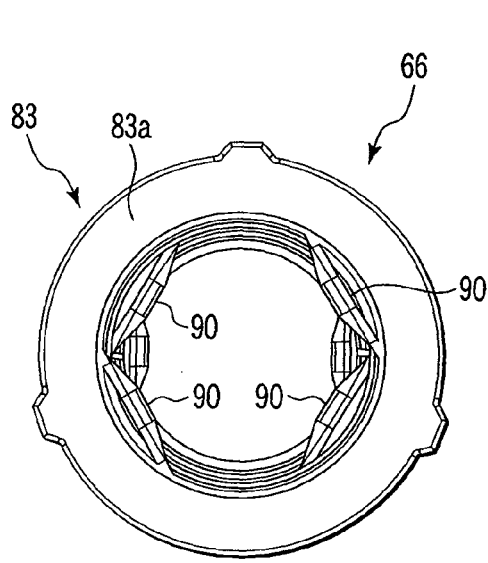
FIG. 44 is a front view showing the electrode hold member of the ultrasonic therapeutic apparatus according to the first embodiment.
Figure 45:
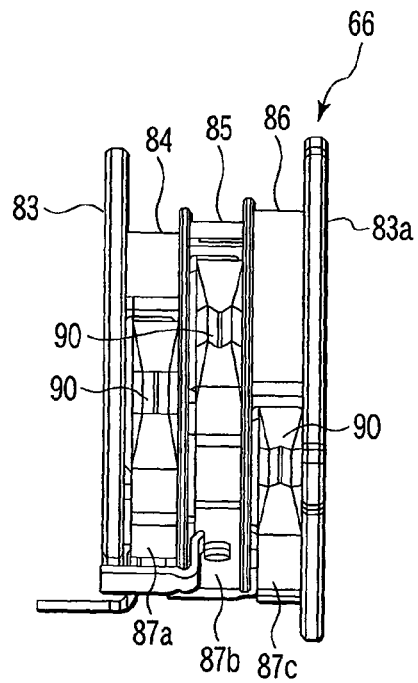
FIG. 45 is a side view showing the electrode hold member of the ultrasonic therapeutic apparatus according to the first embodiment.

FIGS. 43 to 45 show a cylindrical contact-point unit 66 which is assembled to the hold cylinder 48. The contact-point unit 66 includes a cylindrical electrode hold member 83 which is formed of a resin. As shown in FIG. 45, the electrode hold member 83 includes three (first to third) electrode receiving sections 84, 85 and 86 with different outside diameters. The first electrode receiving section 84 on the distal end side has a smallest diameter, and the third electrode receiving section 86 on the rear end side has a greatest diameter.

Figure 48:
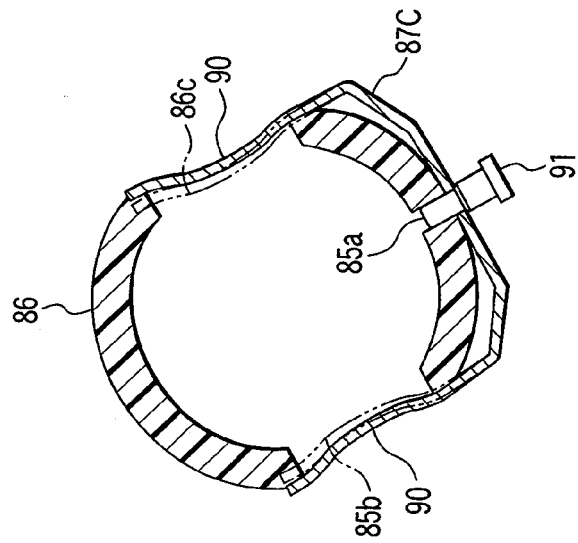
FIG. 48 is a cross-sectional view taken along line 48-48 in FIG. 37.
Figure 47:
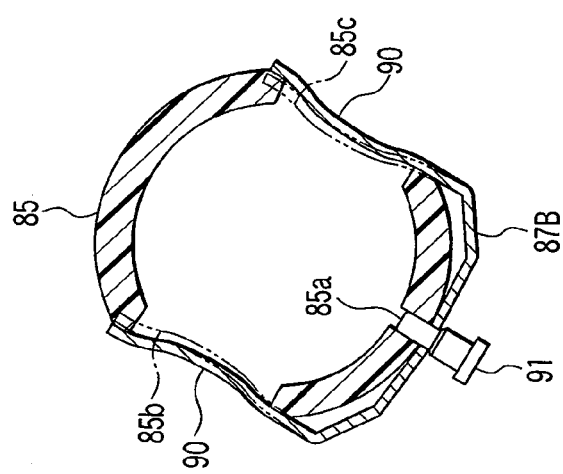
FIG. 47 is a cross-sectional view taken along line 47-47 in FIG. 37.
Figure 46:
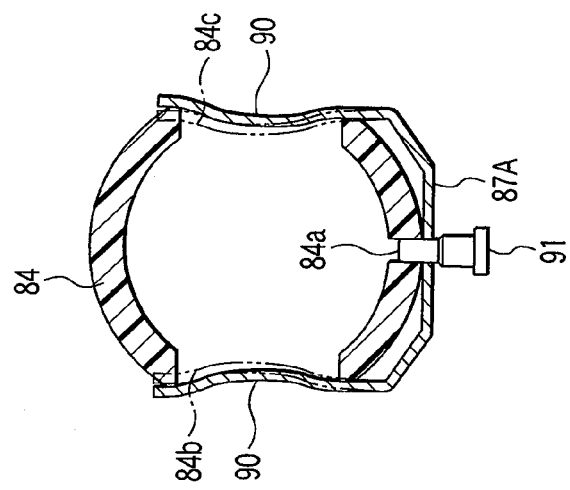
FIG. 46 is a cross-sectional view taken along line 46-46 in FIG. 37.

FIG. 46 shows the first electrode receiving section 84, FIG. 47 shows the second electrode receiving section 85, and FIG. 48 shows the third electrode receiving section 86.

As shown in FIG. 46, the first electrode receiving section 84 has one contact-point member fixing hole 84*a*, and two through-holes 84*b* and 84*c*. A center line of the two through-holes 84*b* and 84*c* is set to be perpendicular to a center line of the contact-point member fixing hole 84*a*.

Similarly, as shown in FIG. 47, the second electrode receiving section 85 has one contact-point member fixing hole 85*a*, and two through-holes 85*b* and 85*c*. As shown in FIG. 48, the third electrode receiving section 86 has one contact-point member fixing hole 86*a*, and two through-holes 86*b* and 86*c*.

The positions of the contact-point member fixing hole 84*a* of the first electrode receiving section 84, the contact-point member fixing hole 85*a* of the second electrode receiving section 85 and the contact-point member fixing hole 86*a* of the third electrode receiving section 86 are displaced in the circumferential direction of the electrode hold member 83.

Figure 49:
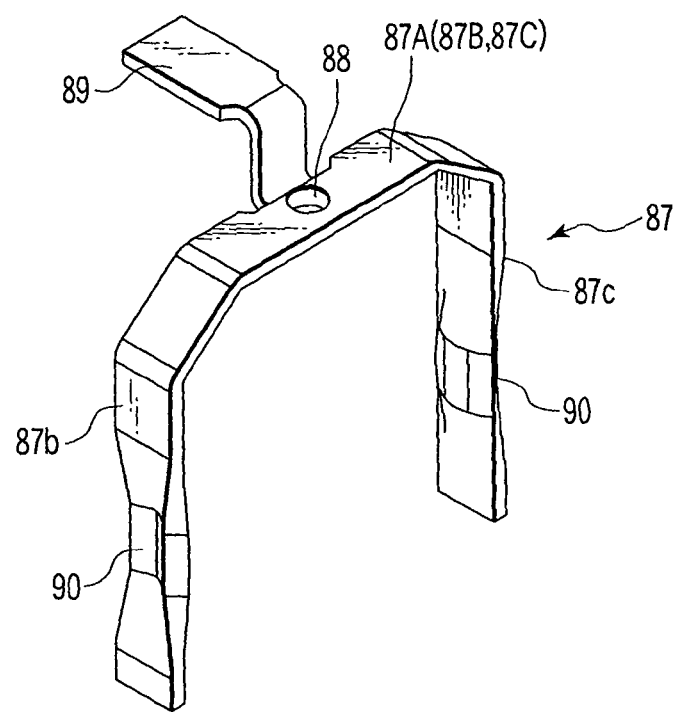
FIG. 49 is a perspective view showing an electrode member of the ultrasonic therapeutic apparatus according to the first embodiment.
Figure 50:
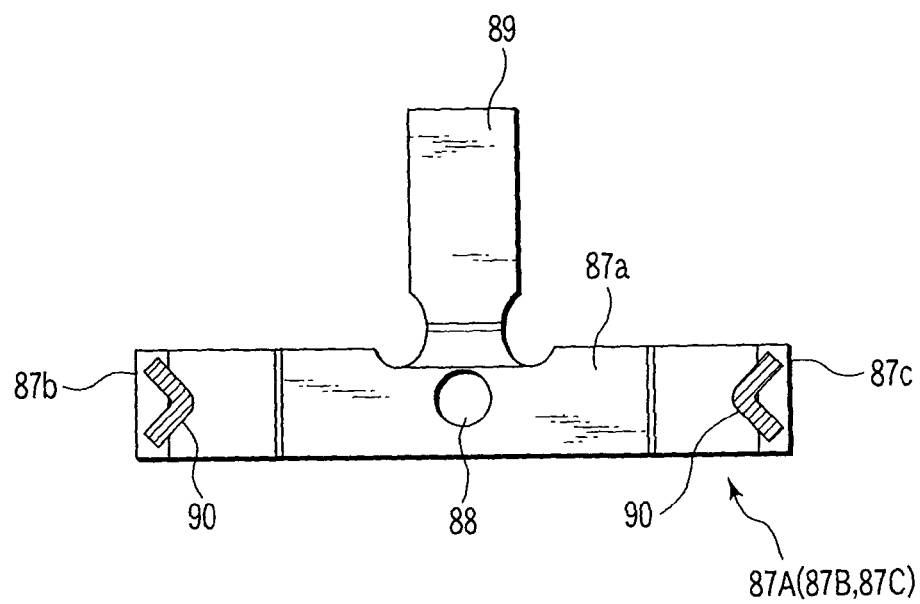
FIG. 50 is a transverse cross-sectional view showing the electrode member of the ultrasonic therapeutic apparatus according to the first embodiment.
Figure 53:
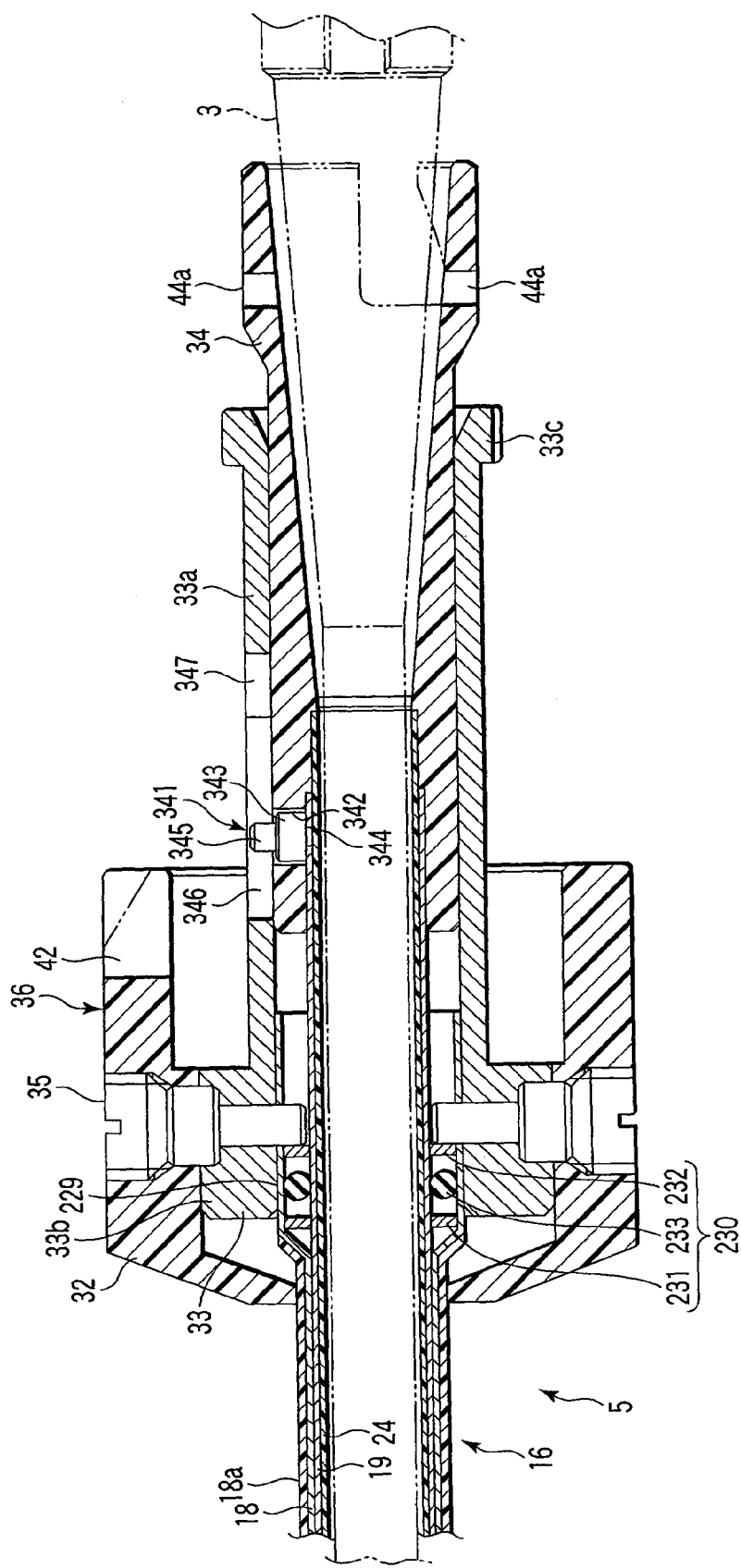
FIG. 53 is a transverse cross-sectional view showing an assembly part of a proximal end portion of a sheath unit of an ultrasonic therapeutic apparatus according to a second embodiment of the present invention.

FIG. 49 and FIG. 50 show electrode members 87A, 87B and 87C which are assembled to the first to third electrode receiving sections 84, 85 and 86. These electrode members 87A, 87B and 87C are formed in the same shape. In the description below, only the electrode member 87A, which is assembled to the first electrode receiving section 84, is described. The common parts of the electrode members 87B and 87C of the other second and third electrode receiving sections 85 and 86 are denoted by like reference numerals, and a description thereof is omitted.

The electrode member 87A includes one straight stationary portion 87*a* and two bend portions 87*b* and 87C. One bend portion 87*b* is disposed at one end of the straight stationary portion 87*a*, and the other bend portion 87*c* is disposed at the other end of the straight stationary portion 87*a*. Thereby, as shown in FIG. 49, the electrode member 87A is formed and bent in a substantially U shape.

A hole 88 and an L-shaped wiring connection portion 89 are provided at a central position of the stationary portion 87*a*. Inwardly curved waist portions 90 are formed at central positions of the two bend portions 87*b* and 87*c*.

When the first electrode receiving section 84 and the electrode member 87A are assembled, a fixing pin 91 is inserted in the hole 88 of the stationary portion 87*a* of the electrode member 87A and in the contact-point member fixing hole 84*a* of the first electrode receiving section 84. The electrode member 87A is fixed to the first electrode receiving section 84 by the fixing pin 91. At this time, the waist portion 90 of one bend portion 87*b* of the electrode member 87A is disposed in one through-hole 84b of the first electrode receiving section 84, and the waist portion 90 of the other bend portion 87c of the electrode member 87A is disposed in the other through-hole 84c. The same applies when the electrode member 87B is assembled to the second electrode receiving section 85 and the electrode member 87C is assembled to the third electrode receiving section 86.

Figure 51:
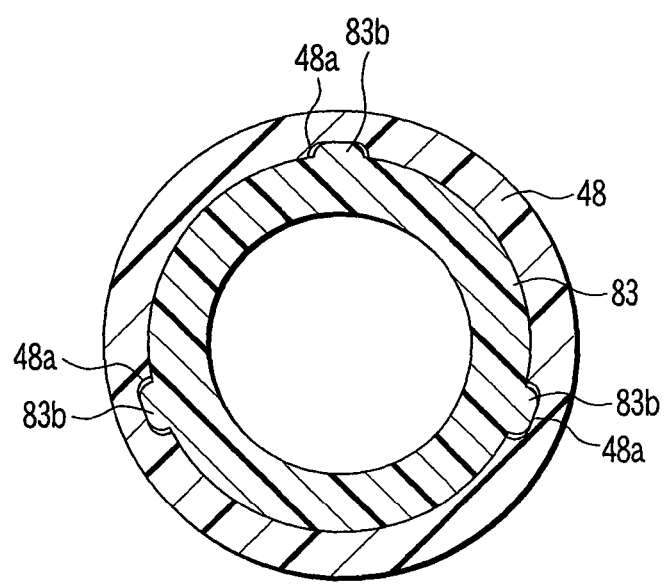
FIG. 51 is a cross-sectional view taken along line 51-51 in FIG. 37.

As shown in FIG. 51, a large-diameter fixing flange portion 83a is formed at a rear end portion of the electrode hold member 83 of the contact-point unit 66. Engaging projection portions 83b are provided to project from the outer peripheral surface of the fixing flange portion 83a at a plurality of locations, for example, at three locations in this embodiment. Engaging recess portions 48a are formed in an inner peripheral surface of the rear end portion of the hold cylinder 48 at positions corresponding to the three engaging projection portions 83b of the stationary flange portion 83a. In the case where the electrode hold member 83 is assembled in the hold cylinder 48, the three engaging projection portions 83b of the stationary flange portion 83a are inserted, engaged and fixed in the engaging recess portions 48a of the hold cylinder 48. Thereby, the rotation of the electrode hold member 83 about the axis thereof, relative to the hold cylinder 48, is restricted.

A stepped portion 43b, which comes in contact with the fixing flange portion 83a of the electrode hold member 83, is formed on the hold cylinder 48. The electrode hold member 83 is fixed to the hold cylinder 48 by a fixing screw 48c in the state in which the fixing flange portion 83a of the electrode hold member 83 abuts upon the stepped portion 43b. Thereby, the axial movement of the electrode hold member 83, relative to the hold cylinder 48, is restricted.

End portions of three wiring lines 93a to 93c, which are assembled in the switch hold section 51, are connected to the wiring connection portions 89 of the three electrode members 87A, 87B and 87C that are assembled to the contact-point unit 66.

Further, as shown in FIG. 42, the contact-point unit 66 is provided with a substantially C-shaped electric contact-point member 96 which is formed of a metallic plate spring. The electric contact-point member 96 is connected to the outer-peripheral surface of the proximal end portion of the spring receiving member 64.

The handle-unit-side electric path 95 is composed of the electrical contact member 96, spring receiving member 64, positioning pin 81 and rotation transmission member 71.

A front end portion of the transducer unit 2 is detachably coupled to the contact-point unit 66. As shown in FIG. 52, two wiring lines 101 and 102 for the ultrasonic transducer, two wiring lines 103 and 104 for high-frequency power and three wiring lines 105, 106 and 107, which are connected to a wiring circuit board within the switch hold section 51, are assembled in the single cable 9 at the rear end of the transducer unit 2. Distal end portions of the two wiring lines 101 and 102 for the ultrasonic transducer are connected to the ultrasonic transducer 6. A distal end portion of one wiring line 103 for high-frequency power is connected to the ultrasonic transducer 6.

First to fourth electrically conductive plates 111 to 114 for electric connection are provided at the rear end of the transducer unit 2. A distal end portion of the other wiring line 104 for high-frequency power is connected to the first conductive plate 111. The three wiring lines 105, 106 and 107 are connected to the second to fourth conductive plates 112 to 114.

FIG. 4 shows the internal structure of a front end portion of the transducer unit 2. A connection cylindrical portion 121 is formed at the distal end portion of the transducer cover 7. A C-ring 122 having a partly cut-out annular plate shape is mounted on the outer peripheral surface of the connection cylindrical body 121. Three (first to third) cylindrical portions 123 to 125 with different outside diameters are projectingly provided on the inside of the connection cylindrical portion 121. The first cylindrical portion 123 has a smallest outside diameter and has a greatest length of projection from the distal end of the connection cylindrical body 121. The second cylindrical portion 124 has an outside diameter, which is greater than the outside diameter of the first cylindrical portion 123, and has a length of projection from the distal end of the connection cylindrical body 121, which is less than the length of projection of the first cylindrical portion 123. The third cylindrical portion 125 has a greatest outside diameter and has a length of projection from the distal end of the connection cylindrical body 121, which is less than the length of projection of the second cylindrical portion 124.

A first cylindrical contact-point member 131 is mounted on the outer peripheral surface of the first cylindrical portion 123. Similarly, a second cylindrical contact-point member 132 is mounted on the outer peripheral surface of the second cylindrical portion 124, and a third cylindrical contact-point member 133 is mounted on the outer peripheral surface of the third cylindrical portion 125. The second conductive plate 112 is connected to the first contact-point member 131, the third conductive plate 113 is connected to the second contact-point member 132, and the fourth conductive plate 114 is connected to the third contact-point member 133.

A fourth contact-point member 134 is mounted on the inner peripheral surface of the first cylindrical body 123. The fourth contact-point member 134 is connected to the first conductive plate 111.

When the handle unit 4 and the transducer unit 2 are coupled, the contact-point unit 66 of the handle unit 4 and the front end portion of the transducer unit 2 are connected. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected.

Next, the operation of the present embodiment is described. The handpiece 1 of the ultrasonic therapeutic apparatus of the present embodiment, as shown in FIG. 2, comprises four units, namely, the transducer unit 2, probe unit 3, handle unit 4 and sheath unit 5, which are detachable. When the handpiece 1 is used, the transducer unit 2 and the probe unit 3 are coupled. Thereby, the first high-frequency electric path 13, which transmits a high-frequency current to the coupled body of the transducer unit 2 and probe unit 3, is formed.

Subsequently, the handle unit 4 and the sheath unit 5 are coupled. When the handle unit 4 and sheath unit 5 are coupled, the connection tube body 34 is inserted in the rotation transmission member 71 of the handle unit 4 in the state in which the handle member 32 of the sheath unit 5 is held. When the sheath unit 5 and handle unit 4 are coupled, the engaging lever 43 on the handle unit 4 side is held in the state in which the engaging lever 43 rests on the inclined surface of the guide groove 41 of the handle member 32 of the sheath unit 5, as shown in FIG. 29 and FIG. 30. At this time, as shown in FIG. 41A, the electrically conductive rubber ring 94b is held in the positional state in which the inner peripheral surface shape of the electrically conductive rubber ring 94b corresponds to the engaging portion 46 of the connection flange portion 33*c*, that is, in the state in which the three corner portions 46*b* of the connection flange portion 33*c* correspond in position to the three corner portions 94*b*2 of the electrically conductive rubber ring 94*b*. Accordingly, the connection flange portion 33*c* of the sheath unit 5 is inserted straight into the electrically conductive rubber ring 94*b*. At the time of this insertion operation, as shown in FIG. 41A, the conductive rubber ring 94*b* is held in the natural, non-compressed position. In this state, the sheath-unit-side electric path 40 and the handle-unit-side electric path 95 are not electrically connected.

Subsequently, following this insertion operation, the handle member 32 of the sheath unit 5 is rotated about the axis thereof, relative to the handle unit 4. By this operation, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94*b* is switched to the pressure contact position where the electrically conductive rubber ring 94*b* is put in pressure contact with the three corner portions 46*b* of the connection flange portion 33*c*. Thereby, the sheath-unit-side electric path 40 and the handle-unit-side electric path 95 are electrically connected via the electrically conductive rubber ring 94*b*. As a result, the second high-frequency electric path 97, which transmits a high-frequency current, is formed in the coupled body of the sheath unit 5 and handle unit 4.

When the sheath unit 5 is rotated about the axis thereof, the pair of engaging pins 45 on the handle unit 4 side are, at the same time, disengageably engaged in the engaging groove 44*a* at the terminal end portion of the guide groove 44 of the sheath unit 5. Thereby, the spring receiving member 64 on the handle unit 4 side and the connection tube body 34 on the sheath unit 5 side are coupled via the engaging pins 45. As a result, the operation force on the handle unit 4 side at the time when the movable handle 49 is closed relative to the stationary handle 47 can be transmitted to the driving pipe 19 of the jaw 17 on the sheath unit 5 side. This state is the coupled state between the sheath unit 5 and the handle unit 4.

Thereafter, the coupled body of the sheath unit 5 and handle unit 4 and the coupled body of the ultrasonic transducer 6 and probe unit 3 are assembled as one body. In this assembling work, the contact-point unit 66 of the handle unit 4 is connected to the front end portion of the transducer unit 2. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected. Thereby, the second high-frequency electric path 97 of the coupled body of the sheath unit 5 and handle unit 4 is connected to the wiring line 104 for high-frequency power within the cable 9. Further, the three wiring lines 105, 106 and 107 within the cable 9 are connected to the wiring circuit board within the switch hold section 51. This state is the completion state of the assembly of the handpiece 1.

When the handpiece 1 is used, the movable handle 49 is opened/closed relative to the stationary handle 47. The driving pipe 19 is axially moved in interlock with the operation of the movable handle 49, and the jaw 17 is opened/closed, relative to the probe distal end portion 3*a* of the probe unit 3, in interlock with the advancing/retreating movement of the driving pipe 19 in its axial direction. When the movable handle 49 is closed relative to the stationary handle 47, the driving pipe 19 is pushed forward in interlock with the operation of the movable handle 49. The jaw 17 is rotated and driven (to a closed position) in a direction toward the probe distal end portion 3*a* of the probe unit 3 in interlock with the pushing operation of the driving pipe 19. By the rotation of the jaw 17 to its closed position, a living body tissue is held between the jaw 17 and the probe distal end portion 3*a* of the probe unit 3.

In this state, one of the switch button 54 for coagulation and the switch button 55 for incision, which are provided on the stationary handle 47, is selectively pressed. When the switch button 54 for coagulation is pressed, power is supplied to the first high-frequency electric path 13 for supplying a high-frequency current to the probe distal end portion 3*a* of the probe unit 3 and to the second high-frequency electric path 97 for supplying a high-frequency current to the jaw body 28 of the sheath unit 5. Thereby, the two bipolar electrodes for high-frequency therapeutic treatment are constituted by the probe distal end portion 3*a* of the probe unit 3 and the jaw body 28 of the sheath unit 5. By supplying a high-frequency current between the two bipolar electrodes which are constituted by the probe distal end portion 3*a* of the probe unit 3 and the jaw body 28 of the sheath unit 5, bipolar high-frequency therapeutic treatment can be performed for the living body tissue between the jaw 17 and the probe distal end portion 3*a* of the probe unit 3.

When the switch button 55 for incision is pressed, a driving current is supplied to the ultrasonic transducer 6 at the same time as the supply of high-frequency current, and the ultrasonic transducer 6 is driven. At this time, ultrasonic vibration from the ultrasonic transducer 6 is transmitted to the probe distal end portion 3*a* via the vibration transmission member 11. Thereby, incision, resection, etc. of the living body tissue can be performed by making use of ultrasonic at the same time as the supply of high-frequency current. In the meantime, coagulation for the living body tissue can be performed by using ultrasonic.

When the movable handle 49 is opened relative to the stationary handle 47, the driving pipe 19 is pulled to the proximal side in interlock with the opening operation of the removable handle 49. The jaw 17 is driven (to an open position) in a direction away from the probe distal end portion 3*a* of the probe unit 3 in interlock with the pulling operation of the driving pipe 19.

When the rotational operation knob 50 is rotated, the rotational movement of the rotation transmission member 71, which rotates together with the rotational operation knob 50, is transmitted to the spring receiving member 64 side via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob 50 as one body about the axis thereof. Further, the rotational operation force of the rotational operation knob 50 is transmitted to the vibration transmission member 11 of the probe unit 3 via the tubular member 98 that rotates together with the spring receiving member 64 within the hold cylinder 48. Thereby, the assembly unit within the hold cylinder 48 and the coupled body of the transducer unit 2 and probe unit 3 are rotated about the axis as one body.

At this time, the handle member 32 and guide cylindrical body 33 of the sheath unit 5 rotate together with the rotational operation knob 50. Furthermore, the sheath 18 rotates together with the guide cylindrical body 33, and the rotation of the guide cylindrical body 33 is transmitted to the connection tube body 34 and driving pipe 19 via the threaded pin 235. Thus, the jaw 17 and probe distal end portion 3a of the therapeutic section 1A are rotated about the axis at the same time together with the rotational operation knob 50.

The following advantageous effects can be obtained by the above-described structure. Specifically, in the handpiece 1 of the ultrasonic therapeutic apparatus according to the present embodiment, as shown in FIG. 28, the threaded pin 235 is fixed to the proximal end portion of the driving pipe 19. The threaded pin 235 is screwed in and passed through the threaded hole portion 237 of the connection tube body 34, and the coupling body 240 which couples the driving pipe 19 and the connection tube body 34 is constituted. Further, the guide cylindrical body 33 is fitted on the flare portion 229 of the proximal end portion of the sheath 18. The large-diameter portion 236b of the threaded pin 235 is engaged with the slit 234 of the guide cylindrical body 33. Thereby, the coupling body 240 is coupled so as to be movable as one body, relative to the guide cylindrical body 33, along the slit 234 in the axial direction of the sheath 18. At this time, the three components, i.e. the driving pipe 19, connection tube body 34 and guide cylindrical body 33, are coupled by the threaded pin 235 in the state in which rotation about the axis of the sheath 18 is prevented.

Thus, according to the present embodiment, the three components, i.e. the driving pipe 19, connection tube body 34 and guide cylindrical body 33, can be coupled by the threaded pin 235 such that the coupling body 240 is movable as one body, relative to the guide cylindrical body 33, along the slit 234 in the axial direction of the sheath 18. Moreover, the three components, i.e. the driving pipe 19, connection tube body 34 and guide cylindrical body 33, can be coupled by the threaded pin 235 in the state in which rotation about the axis of the sheath 18 is prevented. Therefore, the number of structural parts within the hold cylinder 48 of the handle unit 4 can be reduced, compared to the case in the prior art in which the sheath attachment/detachment section for detachably coupling the proximal end portion of the sheath 18 to the stationary handle 47 and the driving member attachment/detachment section for detachably coupling the proximal end portion of the driving member for driving the jaw 17 to the movable handle 49 are independently provided. Thereby, the internal structure of the hold cylinder 48 of the handle unit 4 can be simplified, the assembly work can be facilitated, and the manufacturing cost can be reduced.

Besides, the guide cylindrical body 33 includes the connection flange portion (first attachment/detachment section) 33c which is used at the time of attachment/detachment to/from the handle unit 4 side. The two guide grooves (second attachment/detachment section) 44, which are detachably coupled to the movable handle 49, are provided in the proximal end portion of the connection tube body 34. Thereby, the number of structural parts within the hold cylinder 48 of the handle unit 4 can be reduced, compared to the case in the prior art in which the sheath attachment/detachment section for detachably coupling the proximal end portion of the sheath 18 to the stationary handle 47 and the driving member attachment/detachment section for detachably coupling the proximal end portion of the driving member for driving the jaw 17 to the movable handle 49 are independently provided. Therefore, the internal structure of the hold cylinder 48 of the handle unit 4 can be simplified.

The proximal end portion of the sheath 18 includes the flare portion 229 which has a greater inside diameter than the other portion. The seal means 230 for effecting sealing between the sheath 18 and the driving pipe 19 is provided between the flare portion 229 and the driving pipe 19. Thereby, even in the case where the handpiece 1 is used in such an environment of an endoscopic surgical operation that the body cavity is insufflated, an insufflated gas, for instance, which has come in from between the sheath 18 and the driving pipe 19, is prevented from entering the inside of the handle unit 4. Therefore, the airtightness of the inside of the handle unit 4 can be ensured at low cost.

The seal means 230 includes the backup rings 231 and 232, which are paired in a back-and-forth direction along the axis of the sheath 18, and the O ring 233 which is provided between the backup rings 231 and 232 so as to be movable in the axial direction of the sheath 18. Thereby, the airtightness can be secured while the sliding resistance by the O ring 233 is reduced.

The connection tube body 34 has the threaded hole portion 237 in which the threaded pin 235 is inserted. The threaded pin 235 has the male screw portion 236a which is screwed and engaged in the threaded hole portion 237. Thereby, the male screw portion 236a of the threaded pin 235 is screwed and inserted through the threaded hole portion 237 of the connection tube body 34, and the coupling body 240 of the driving pipe 19 and the connection tube body 34 is constituted. Moreover, the large-diameter portion 236b of the threaded pin 235 is engaged in the slit 234 of the guide cylindrical body 33, and thereby the coupling body 240 is coupled so as to be movable as one body, relative to the guide cylindrical body 33, along the slit 234 in the axial direction of the sheath 18. At this time, the three components, i.e. the driving pipe 19, connection tube body 34 and guide cylindrical body 33, are coupled in the state in which rotation about the axis of the sheath 18 is prevented. Therefore, the internal structure of the hold cylinder 48 of the handle unit 4 can be simplified, the assembly work can be facilitated, and the manufacturing cost can be reduced.

FIG. 53 to FIG. 56 show a second embodiment of the ultrasonic therapeutic apparatus of the present invention. In this embodiment, the structure of the assembly part of the proximal end portion of the sheath unit 5 of the ultrasonic therapeutic apparatus of the first embodiment (see FIG. 1 to FIG. 52) is altered as follows.

Specifically, in this embodiment, the threaded pin 235 in the first embodiment is replaced with a top-shaped pin 341, by which the three components, i.e. the driving pipe 19, connection tube body 34 and guide cylindrical body 33, are coupled.

A circular hole 342 with no thread, which is substituted for the threaded hole portion 237 in the first embodiment, is formed in the connection tube body 34.

Figure 55:
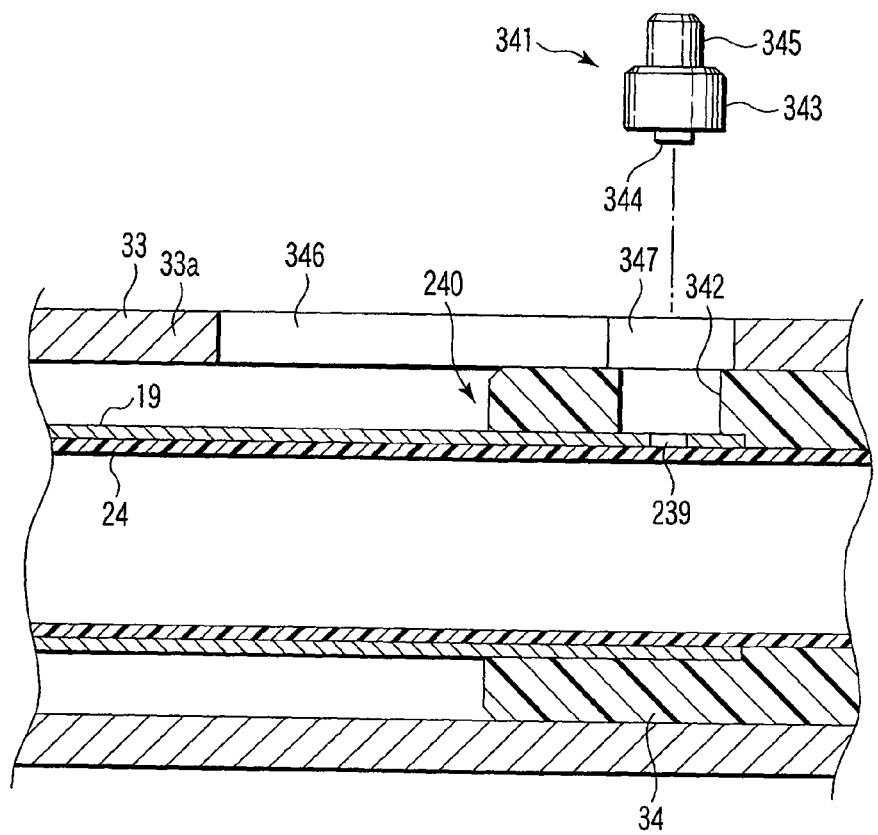
FIG. 55 is a transverse cross-sectional view showing a state before the top-shaped pin is assembled to the assembly part of the proximal end portion of the sheath unit of the ultrasonic therapeutic apparatus according to the second embodiment.

As shown in FIG. 55, the top-shaped pin 341 includes a first press-fitting portion 343 having a columnar shape, a second press-fitting portion 344 which projects from one end portion of the first press-fitting portion 343, and a columnar engaging portion 345 which projects from the other end portion of the first press-fitting portion 343. The first press-fitting portion 343 is formed to have such a size as to permit press-fitting in the circular hole 342 of the connection tube body 34. The second press-fitting portion 344 is formed to have such a size as to permit press-fitting in a fixing hole 239 in the driving pipe 19. The engaging portion 345 is formed to have a smaller diameter than the first press-fitting portion 343.

The outer peripheral wall portion of the guide cylindrical body 33 has an elongated slit 346 extending in the axial direction of the sheath 18. The groove width of the slip 346 is set to be substantially equal to the diameter of the engaging portion 345 of the top-shaped pin 341. The engaging portion 345 of the top-shaped pin 341 is engaged in the slit 346 so as to be movable along the slit 346 in the axial direction of the sheath 18. A circular hole 347, which has a greater diameter than the width of the slit 346, is continuously formed at the proximal end portion of the slit 346. The circular hole 347 is set to have such a size as to permit insertion of the second press-fitting portion 344 of the top-shaped pin 341.

When the three components, i.e. the driving pipe 19, connection tube body 34 and guide cylindrical body 33, are coupled, the following operation is performed. To begin with, the connection tube body 34 is inserted from the rear side into the guide cylindrical body 33. Further, the driving pipe 19 is set in the state in which the driving pipe 19 is inserted from the front side into the connection tube body 34. At this time, as shown in FIG. 55, the circular hole 347 of the guide cylindrical body 33, the circular hole 342 of the connection tube body 34 and the fixing hole 239 of the driving pipe 19 are overlapped and aligned.

Figure 54:
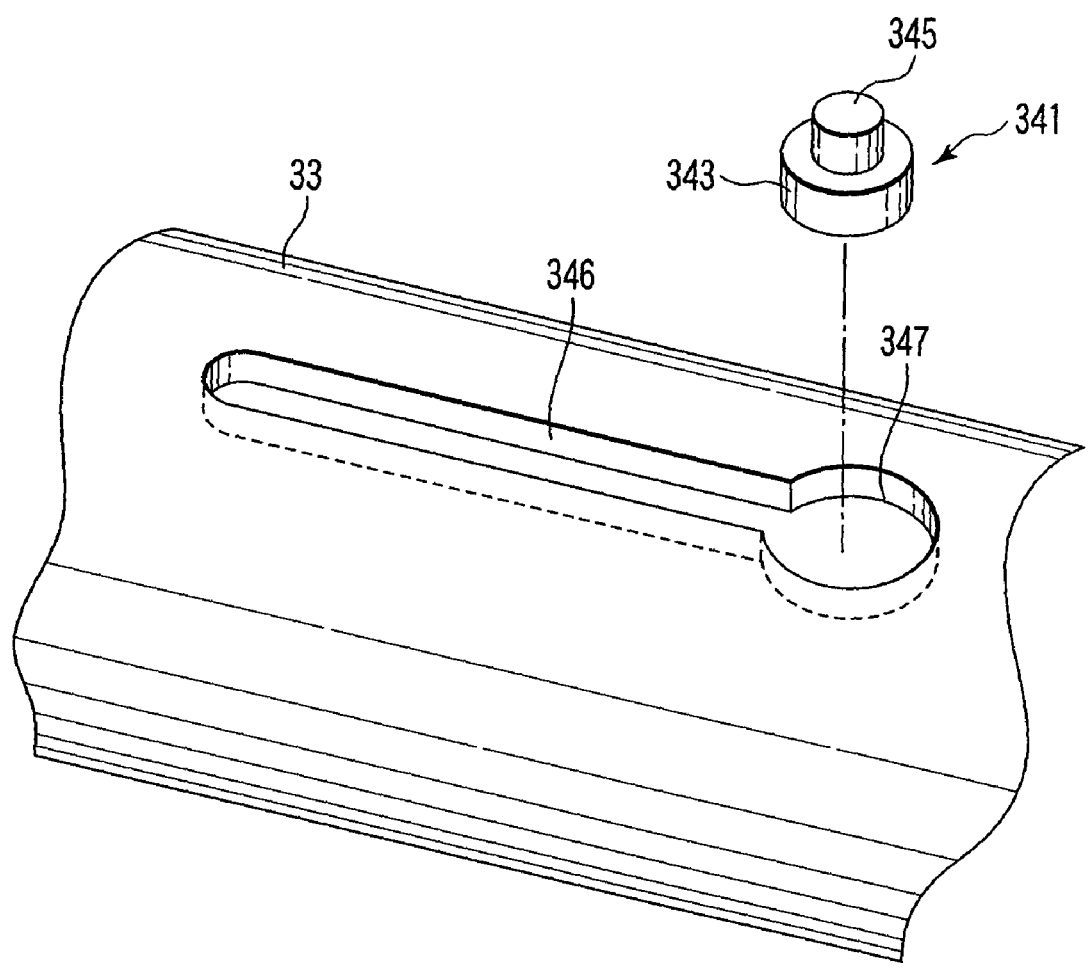
FIG. 54 is a perspective view showing a state before a top-shaped pin is assembled to the assembly part of the proximal end portion of the sheath unit of the ultrasonic therapeutic apparatus according to the second embodiment.

Subsequently, as shown in FIG. 54, the top-shaped pin 341 is inserted, from the second press-fitting portion 344 thereof, into the circular hole 347 of the guide cylindrical body 33. When the top-shaped pin 341 is inserted, the second press-fitting portion 344 of the top-shaped pin 341 is press-fitted in the fixing hole 239 of the driving pipe 19 through the circular hole 347 of the guide cylindrical body 33 and the circular hole 342 of the connection tube body 34. At the same time, the first press-fitting portion 343 of the top-shaped pin 341 is press-fitted in the circular hole 342 of the connection tube body 34 through the circular hole 347 of the guide cylindrical body 33. Thereby, the coupling body 240 in which the driving pipe 19 and the connection tube body 34 are coupled is formed via the top-shaped pin 341.

Figure 56:
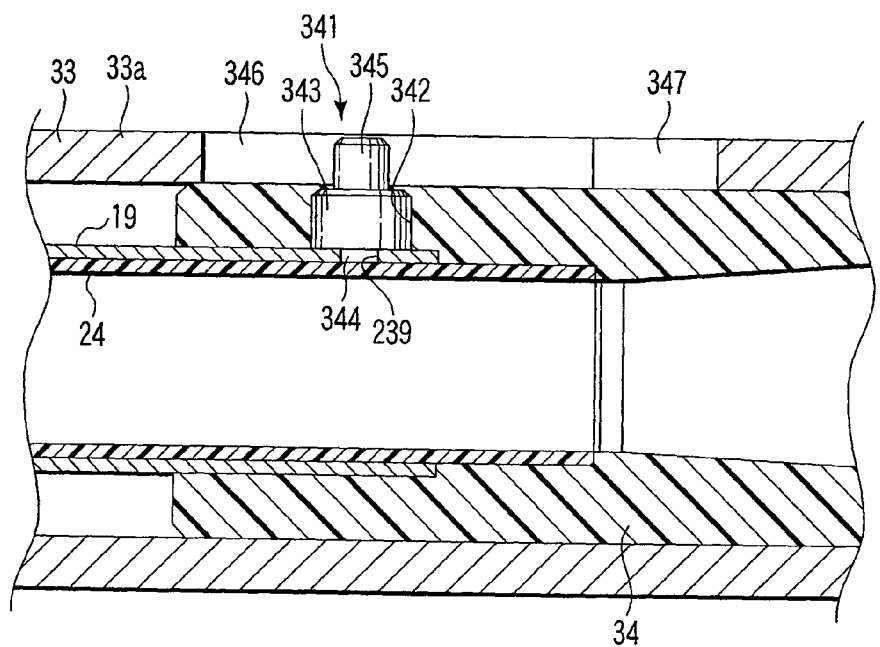
FIG. 56 is a transverse cross-sectional view showing a state in which the top-shaped pin is assembled to the assembly part of the proximal end portion of the sheath unit of the ultrasonic therapeutic apparatus according to the second embodiment.

Thereafter, as shown in FIG. 56, the engaging portion 345 of the top-shaped pin 341 is moved until the engaging portion 345 is inserted in the slit 346. Thus, in the state in which the movement of the engaging portion 345 of the top-shaped pin 341 is guided along the slit 346, the coupling body 240 is coupled so as to be movable as one body, relative to the guide cylindrical body 33, in the axial direction of the sheath 18. At this time, the three components, i.e. the driving pipe 19, connection tube body 34 and guide cylindrical body 33, are coupled in the state in which rotation about the axis of the sheath 18 is prevented. Thereby, the three components, i.e. the driving pipe 19, connection tube body 34 and guide cylindrical body 33, are coupled in the state in which axial movement between the coupling body 240 and the guide cylindrical body 33 is permitted while rotation in the diametrical direction is prevented.

The following advantageous effects can be obtained by the above-described structure. Specifically, in the handpiece 1 of the ultrasonic therapeutic apparatus of the present embodiment, as shown in FIG. 56, the top-shaped pin 341 is fitted and fixed in the proximal end portion of the driving pipe 19. The top-shaped pin 341 is press-fitted and inserted through the circular hole portion 342 of the connection tube body 34, and the coupling body 240 which couples the driving pipe 19 and the connection tube body 34 is constituted. Further, the guide cylindrical body 33 is fitted on the flare portion 229 of the proximal end portion of the sheath 18. The engaging portion 345 of the top-shaped pin 341 is engaged in the slit 346 of the guide cylindrical body 33. Thereby, the coupling body 240 is coupled so as to be movable as one body, relative to the guide cylindrical body 33, along the slit 346 in the axial direction of the sheath 18. At this time, the three components, i.e. the driving pipe 19, connection tube body 34 and guide cylindrical body 33, are coupled by the top-shaped pin 341 in the state in which rotation about the axis of the sheath 18 is prevented.

Therefore, according to the present embodiment, the three components, i.e. the driving pipe 19, connection tube body 34 and guide cylindrical body 33, can be coupled by the top-shaped pin 341 such that the coupling body 240 is movable as one body, relative to the guide cylindrical body 33, along the slit 236 in the axial direction of the sheath 18. Further, the three components, i.e. the driving pipe 19, connection tube body 34 and guide cylindrical body 33, can be coupled by the top-shaped pin 341 in the state in which rotation about the axis of the sheath 18 is prevented. Hence, the number of structural parts within the hold cylinder 48 of the handle unit 4 can be reduced, compared to the case in the prior art in which the sheath attachment/detachment section for detachably coupling the proximal end portion of the sheath 18 to the stationary handle 47 and the driving member attachment/detachment section for detachably coupling the proximal end portion of the driving member for driving the jaw 17 to the movable handle 49 are independently provided. Thereby, the internal structure of the hold cylinder 48 of the handle unit 4 can be simplified, the assembly work can be facilitated, and the manufacturing cost can be reduced.

Moreover, in the present embodiment, the connection tube body 34 has the circular hole 347, and the top-shaped pin 341 has the first press-fitting portion 343 that is press-fitted in the circular hole 347. The first press-fitting portion 343 of the top-shaped pin 341 is passed through the circular hole 347 of the guide cylindrical body 33 and fitted in the circular hole 342 of the connection tube body 34. Thereby, the coupling body 240 in which the driving pipe 19 and connection tube body 342 are coupled is constituted via the top-shaped pin 341. Therefore, the assembly work can more easily be performed since there is no threaded portion, unlike the first embodiment in which the threaded pin 235 is used.

In the case where the threaded pin 235 is used as in the first embodiment, a certain length of the threaded part is needed in order to secure the assembling strength between the three components. By contrast, in the present embodiment, since there is no threaded part, the assembling strength between the three components can be secured even if the thickness of the guide cylindrical body 33 is reduced. Therefore, there is the advantage that the size of the assembly part between the three components can further be reduced.

Needless to say, the present invention is not limited to the above-described embodiments, and various modifications may be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical operating apparatus comprising:
   a sheath including a distal end portion and a proximal end portion;
   a shaft-shaped probe body inserted through the sheath and including a distal end portion and a proximal end portion, and in which ultrasonic vibration is adopted to be transmitted;
   a probe distal end portion provided at the distal end portion of the probe body;
   a jaw rotatably supported on the distal end portion of the sheath and configured to be engaged with the probe distal end portion;

a first tubular member including a tubular body wherein the tubular body is fitted on the proximal end portion of the sheath, extends rearward, and includes an elongated slit, and the slit is provided in an outer peripheral wall portion of the tubular body and extends in an axial direction of the sheath;

a second tubular member inserted into a rear end portion of the first tubular member slidably in the axial direction of the sheath;

a tubular driving member inserted through the sheath slidably in the axial direction of the sheath, and configured to rotate the jaw by sliding movement thereof; and a coupling member including a projection body and an engaging portion wherein the projection body projects outward from the driving member and is passed through the second tubular member to form a coupling body in which the driving member and the second tubular member are coupled to each other, and the engaging portion is engaged in the slit of the first tubular member to couple the coupling body to the first tubular member such that the coupling body is slidable as one body, relative to the first tubular member, along the slit in the axial direction of the sheath.

2. The surgical operating apparatus according to claim 1, wherein the surgical operating apparatus includes a handle unit which is detachably coupled to the proximal end portion of the sheath, the handle unit includes a stationary handle and a movable handle which is coupled rotatably about a rotational shaft relative to the stationary handle, the first tubular member includes a first attachment/detachment section which is detachably coupled to the stationary handle, and the second tubular member includes a second attachment/detachment section which is detachably coupled to the movable handle.

3. The surgical operating apparatus according to claim 1, wherein the sheath includes a flare portion at the proximal end portion of the sheath and the flare portion has a greater inside diameter than that of the other portion of the sheath, and a seal mechanism configured to effect sealing between the sheath and the driving member is provided between the flare portion and the driving member.

4. The surgical operating apparatus according to claim 3, wherein the seal mechanism includes a pair of backup rings, which are paired in a back-and-forth direction along the axial direction of the sheath, and an O ring which is provided between the backup rings so as to be movable in the axial direction of the sheath.

5. The surgical operating apparatus according to claim 1, wherein the second tubular member has a through-hole in which the projection body of the coupling member is passed through, and the projection body has a threaded portion which is screwed and coupled in the through-hole.

6. The surgical operating apparatus according to claim 1, wherein the second tubular member has a through-hole in which the projection body of the coupling member is passed through, and the projection body has, at a part of a penetration portion which is passed through the through-hole, a press-fitting portion which is press-fitted in the through-hole.

* * * * *